United States Patent
Roger et al.

(10) Patent No.: US 8,562,823 B2
(45) Date of Patent: Oct. 22, 2013

(54) DYNAMIC WEIGHT BALANCING OF FLOW IN KIDNEY FAILURE TREATMENT SYSTEMS

(71) Applicants: Baxter International Inc., Deerfield, IL (US); Baxter Healthcare S.A., Glattpark (Opfikon) (CH)

(72) Inventors: Rodolfo G. Roger, Clearwater, FL (US); Michael E. Hogard, Odessa, FL (US); Thomas D. Kelly, Highland Park, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/864,921

(22) Filed: Apr. 17, 2013

(65) Prior Publication Data

US 2013/0231607 A1 Sep. 5, 2013

Related U.S. Application Data

(62) Division of application No. 11/422,267, filed on Jun. 5, 2006.

(51) Int. Cl.
| | | |
|---|---|---|
| *B01D 21/24* | (2006.01) | |
| *B01D 27/10* | (2006.01) | |
| *B01D 35/14* | (2006.01) | |
| *B01D 41/00* | (2006.01) | |
| *B01D 21/30* | (2006.01) | |

(52) U.S. Cl.
USPC ............ 210/104; 210/130; 210/133; 210/137

(58) Field of Classification Search
USPC .................. 210/104, 137, 130, 133
See application file for complete search history.

(56) References Cited

U.S. PATENT DOCUMENTS

| | | |
|---|---|---|
| 4,560,472 A | 12/1985 | Granzow et al. |
| 4,684,460 A | 8/1987 | Issautier |
| 5,011,607 A | 4/1991 | Shinzato |

(Continued)

FOREIGN PATENT DOCUMENTS

| | | |
|---|---|---|
| EP | 0824021 | 2/1998 |
| WO | 92/00768 | 1/1992 |
| WO | 93/06875 | 4/1993 |
| WO | PCT/US2007/070074 | 11/2007 |

OTHER PUBLICATIONS

Manns et al., The acu-menTM: A new device for continuous renal replacement therapy in actue renal failure, Kidney International, 1998, pp. 268-274, Vol. 54.

(Continued)

*Primary Examiner* — Bobby Ramdhanie
*Assistant Examiner* — Dirk Bass
(74) *Attorney, Agent, or Firm* — K&L Gates LLP

(57) ABSTRACT

A kidney failure treatment system includes: (i) a dialysate supply; (ii) a weighing device; a control container coupled operably to the weighing device; (iii) a diffusion membrane; (iv) a drain; first and second pumps; (v) a first fluid conduit coupled fluidly to the dialysate supply and the diffusion membrane, the first fluid conduit coupled operably to the first pump; (vi) a second fluid conduit coupled fluidly to the control container and the drain, the second fluid conduit coupled operably to the first pump; and (vii) a third fluid conduit coupled fluidly to the diffusion membrane and the control conduit, the third fluid conduit coupled operably to the second pump.

20 Claims, 18 Drawing Sheets

(56) References Cited

U.S. PATENT DOCUMENTS

| | | |
|---|---|---|
| 5,141,492 A | 8/1992 | Dadson et al. |
| 5,334,139 A | 8/1994 | Jeppsson et al. |
| 5,722,947 A | 3/1998 | Jeppsson et al. |
| 5,782,796 A | 7/1998 | Din et al. |
| 5,928,177 A | 7/1999 | Brugger et al. |
| 6,117,122 A | 9/2000 | Din et al. |
| 6,327,895 B1 | 12/2001 | Jeppsson et al. |
| 6,780,322 B1 | 8/2004 | Bissler et al. |
| 2004/0215129 A1 | 10/2004 | Edgson et al. |
| 2004/0267183 A1 | 12/2004 | Chevallet |
| 2005/0131332 A1 | 6/2005 | Kelly et al. |

OTHER PUBLICATIONS

Operators Manual for Fresenius USA/Delmed 90/2 Peritoneal Dialysis System written by Fresenius USA, Inc. dated Feb. 6, 1991.

"Serena," 1 page, marketing brochure published by Gambro (undated).

"Selectra—Peritoneal Dialysis Machine for CAPD, CCPD, NPD, IPD and Manual Dialysis," 5 pages, marketing brochure written by www.medionics.com, printed on Sep. 28, 2006.

"Microstar—Volumetric Peritoneal Dialysis Cycler," 2 pages, marketing brochure written by www.medionics.com, printed on Sep. 28, 2006.

"Selectra II—Highly Efficient APD Machine for IPD, CCPD, or Tidal Dialysis," 2 pages, marketing brochure written by www.medionics.com, printed on Sep. 28, 2006.

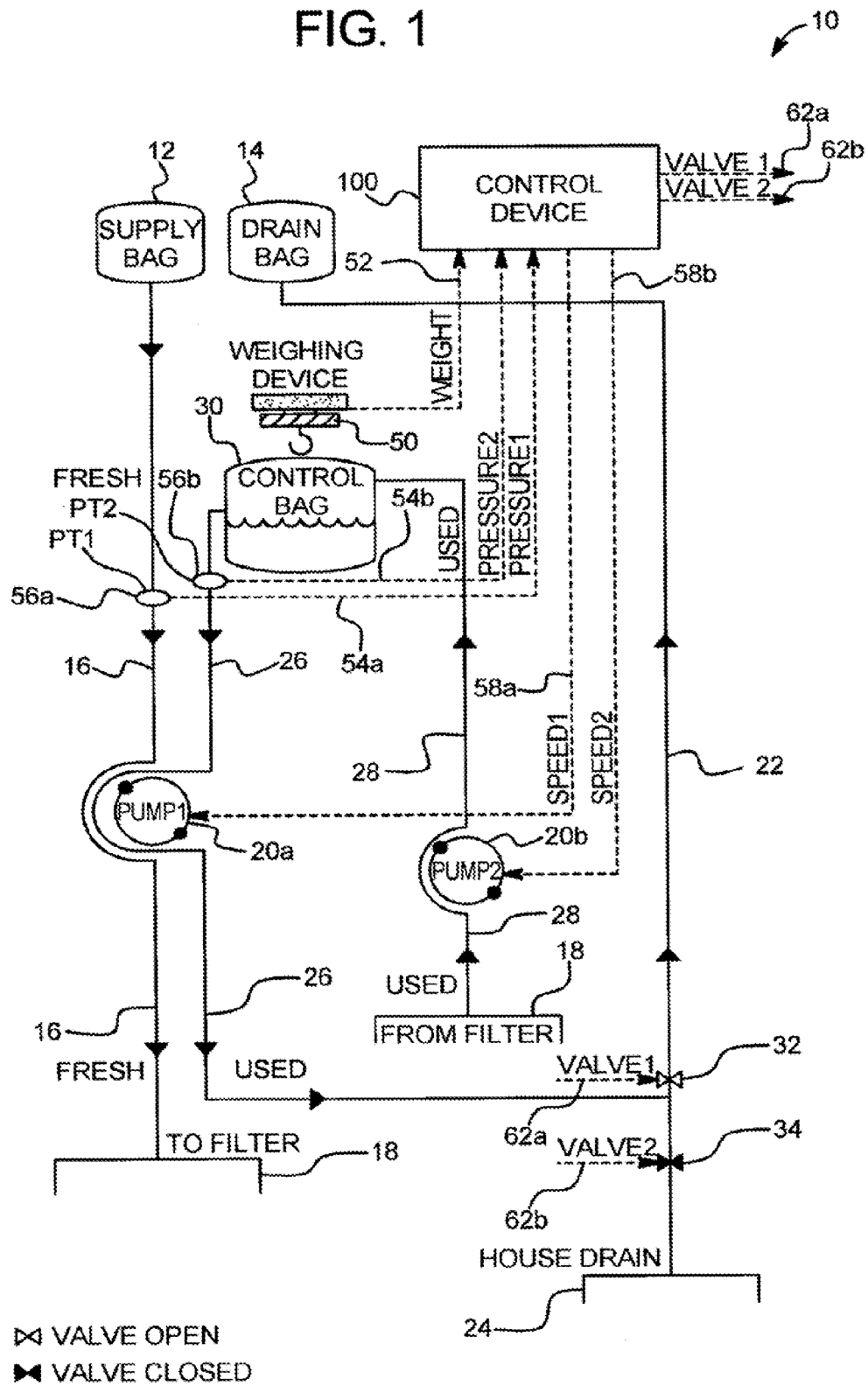

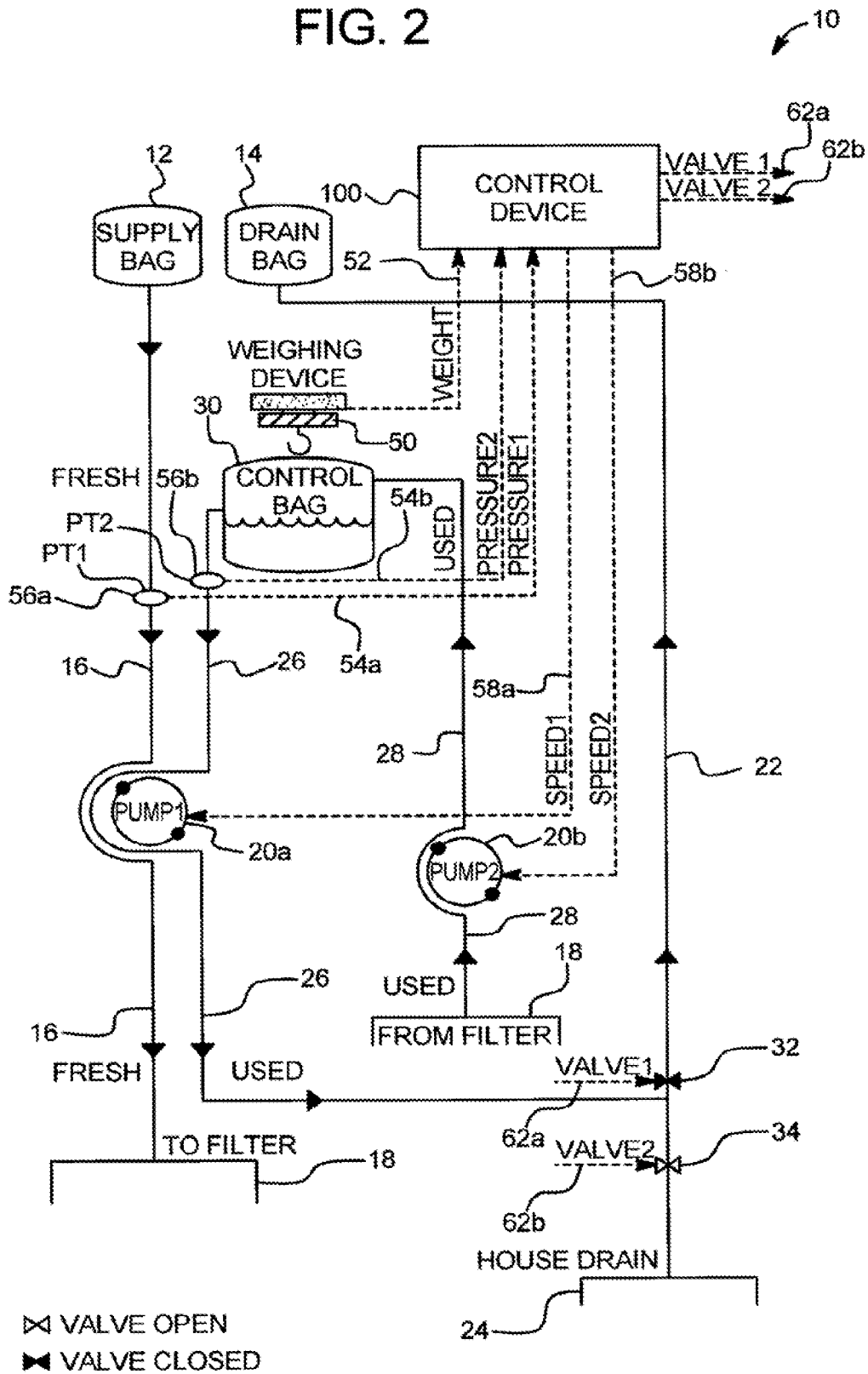

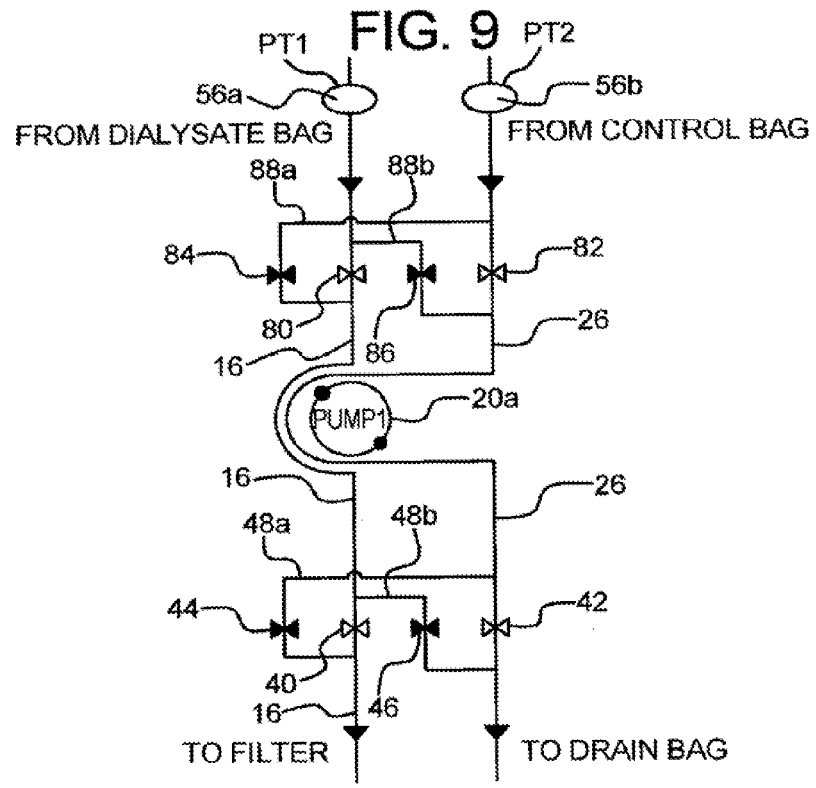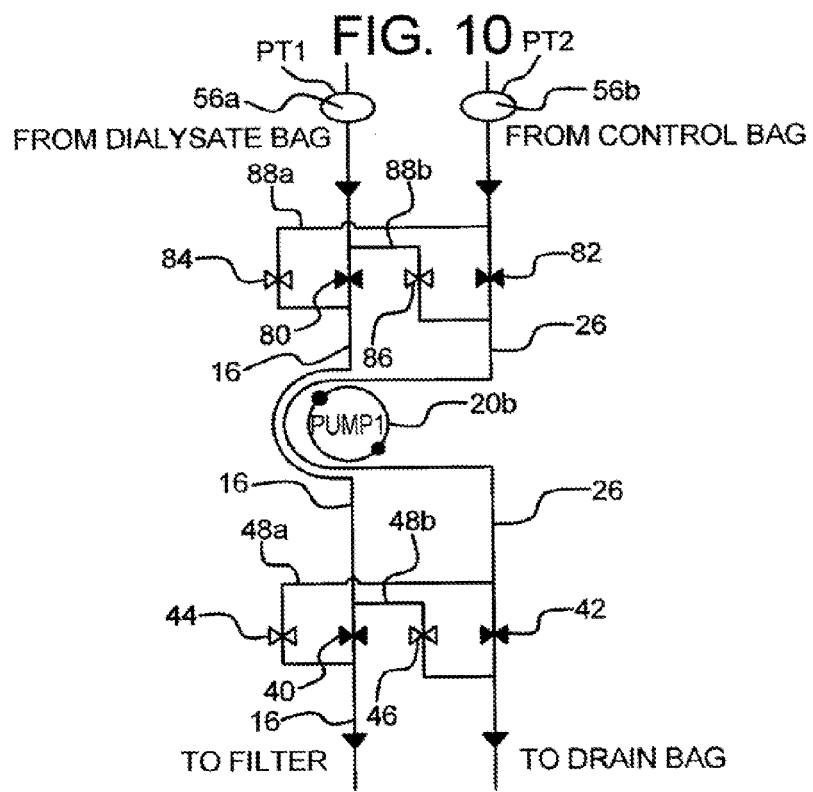

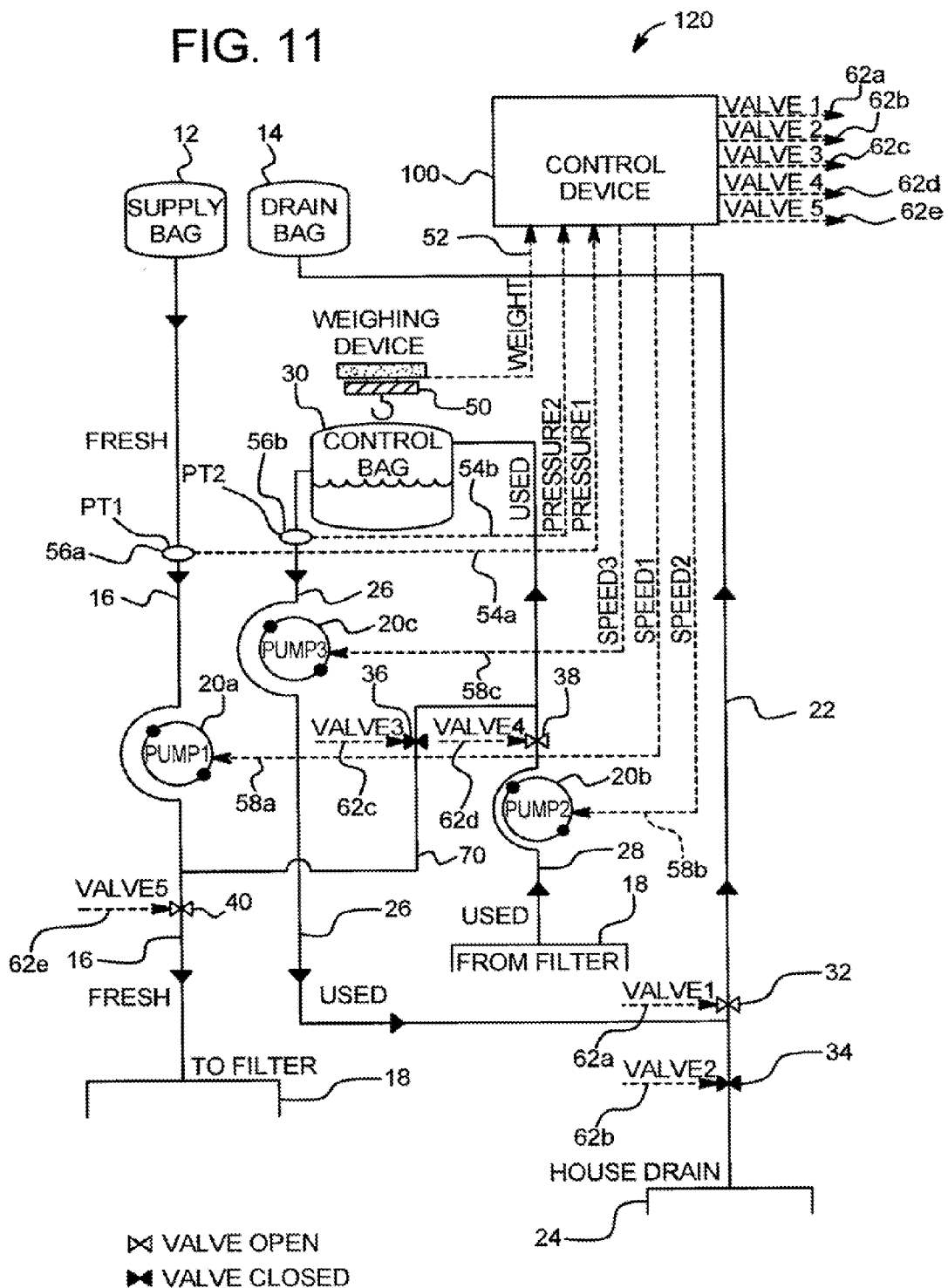

DYNAMIC WEIGHT BALANCING OF FLOW IN KIDNEY FAILURE TREATMENT SYSTEMS

PRIORITY CLAIM

This application is a divisional application of, and claims the benefit of and priority to, U.S. patent application Ser. No. 11/422,267, filed on Jun. 5, 2006, the entire contents of which are incorporated herein by reference.

BACKGROUND

The examples discussed below relate generally to medical fluid delivery. More particularly, the examples disclose systems, methods and apparatuses for the control of fluid flow in kidney failure treatment systems.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to control ulrtrafilltration, which is the process by which water (with electrolytes) moves across a membrane, such as a dialyzer or peritoneal membrane. For example, ultrafiltratrion in HD is a result of transmembrane and osmotic pressure differences between blood and dialysate across a dialyzer membrane. For a given osmotic pressure, the greater the transmembrane pressure the more rapid the ultrafiltration.

People with kidney failure typically retain water and fluids between treatments. That excess fluid needs to be removed during the next treatment. It is important to know how much fluid is removed so that the patient can be returned to their normal weight by the end of therapy. It is also important in some instances to know accurately the rate at which ultrafiltration is taking place at a given time during therapy.

Different systems have been employed to control ultrafiltration. One system described in U.S. Pat. No. 5,247,434 ("the '534 patent"), assigned to the assignee of the present application, the entire contents of which are incorporated expressly herein by reference, controls ultrafiltration volumetrically. The patent describes a volumetrically balanced system that uses first and second chambers of substantially equal volume. Each chamber includes two compartments, one termed a "pre-dialyzer" compartment and the other a "post-dialyzer" compartment. Each opposing "pre" and "post" compartment of a chamber is separated by a flexible diaphragm. Solenoid-actuated valves control the filling and emptying of each compartment. In general, each compartment is completely filled before its contents are discharged. Also, the "pre" compartments are alternately filled and discharged and the "post" compartments are alternately filled and discharged. Filling a "pre" compartment causes a discharge of a corresponding and opposing "post" compartment, respectively. Filling a "post" compartment causes a discharge of a corresponding and opposing "post" compartment.

Since the volumes of opposing "pre" and "post" compartments of the two chambers are equal, the system volumetrically balances the flow of dialysate to and from the dialyzer. One benefit of this volumetrically controlled system is that dialysate flow to the dialyzer can be accurately measured over a wide range of flow rates.

The volumetric system works well for HD machines placed in centers, which produce dialysate online. In HD, the dialysate is not infused into the patient and is therefore not considered a drug. The balancing chambers can therefore be located inside the machine and sterilized between treatments. The same balancing chambers are used over and over.

PD infuses dialysate into the patient's peritoneum. Dialysate for PD is therefore considered a drug, so that the dialysate has to meet sterility requirements for a drug. Anything that comes in contact with the dialysate must also be sterilized and discarded after use. For PD then, at least a component of the balancing chambers would have to be sterilized and disposable, making balancing chambers for PD less attractive from a cost standpoint, compared for example to simple tubing used with peristaltic pumps.

Problems exist with prior fluid control systems employing scales to measure the weight of fluid delivered to and taken from the patient. For example, previous systems employing scales have had to be robust enough to accommodate the total size and weight of the dialysate used during treatment. The load cells of systems have an associated error, which is based on a percentage of the total weight of fluid. As the total weight of the fluid increases, the error increases correspondingly and begins to compromise the accuracy of the system.

Also, because all the bags have to be weighed, a relatively robust mechanical base hanging system has to be provided to handle the associated stresses. Further, the size of the weighing system makes it more prone to interferences from bumps or hits for example. The size of the weighing system can also make storage of the multiple bags difficult, for example, providing a container or support system capable of isolating the weighing system from mechanical interferences and protecting the load cell.

Moreover, multiple supply bags can be complex and difficult for the patient to attach to the weighing system. For example, the multiple bags may have to be lifted to an inconvenient height. Also, in prior gravimetric systems, spent dialysate has to be collected, requiring the operator to carry heavy, full bags of fluid twice, once for setup and again after treatment. A need therefore exists for a simplified and relatively inexpensive fluid control system for kidney failure treatments, which is accurate and easy to maintain.

SUMMARY

The examples described herein disclose dynamic weight or gravimetric balancing medical fluid flow systems and methods applicable for example to: hemodialysis ("HD"), hemofiltration ("HF"), hemodiafiltration ("HDF"), peritoneal dialysis (("PD"), including continuous ambulatory peritoneal dialysis ("CAPD"), automated peritoneal dialysis ("APD"), tidal flow APD and continuous flow peritoneal dialysis ("CFPD") modalities). The systems may also be used in any type of continuous renal replacement therapy ("CRRT"). The examples below include a diffusion membrane or filter, such as a dialyzer, e.g., for HD or HDF, a hemofiliter, e.g., for HF or the patient's peritoneum, e.g., for PD. Moreover, each of the systems described herein may be used in clinical or home settings. For example, the systems may be employed in an in-center HD machine, which runs virtually continuously throughout the day. Alternatively, the systems may be used in a home PD machine, which is typically run at night while the patient is sleeping.

The examples below include a dialysate (replacement fluid) supply, which for convenience is shown as a single bag of the fluid. Alternatively, multiple bags of dialysate supply are ganged together and used one after another. Further alternatively, each of the systems shown below can be used with an online source, such as one or more concentrate pump configured to combine one or more concentrate with water to form dialysate online. Online sources are used commonly with HD systems for example.

In one example, a system and method are provided in which a control container is coupled operably to a weighing device, which communicates with a control device. Two pumps are provided, which can be peristaltic pumps. The first pump drives segments of two different tubes. One tube segment delivers fresh dialysate to an inlet of one of the above-described filters. The other tube segment pulls fluid from the control bag to a drain. The second pump segment pumps fluid from the filter into the control bag. In theory, the fluid volume/rate pumped through the two tubes operable with the same pump head is the same, making the fresh dialysate pumped to the inlet of the filter equal or substantially equal to the spent dialysate pumped from the control bag.

Any difference in weight gained or lost within the control bag therefore corresponds to a net ultrafiltration volume removed from the patient or a net amount of fresh dialysate supplied to the patient, respectively. This system enables both the total amount of fluid removed or added to the patient plus the rate of which such fluid is removed or added to the patient to be known. Accordingly, the system provides a relatively noncomplex and accurate way to monitor a kidney failure therapy, such as HD, and to control the ultrafiltration rate, such as according to a UF profile.

It may be determined that the actual difference in flow through the two pump segments operable with the first pump head is different enough, such that an error detection and/or correction apparatus and method is needed. One such embodiment for detecting an error includes a bypass line connected between the fresh dialysate line (extending from the fresh dialysate supply to the inlet of the filter) to the spent dialysate return line, which operates with the second pump and leads to the control container. The system is valved such that at a desired point and time, the filter is bypassed. That is, fresh dialysate that would normally flow to the filter is sent instead to the control bag. The second pump is not operated, so that no new ultrafiltration is pulled from the filter to the control bag.

In theory, the weight of liquid in the control container should not change over time because the first pump is theoretically pushing in and pulling dialysate to and from the control bag at the same rate. A detected increase or decrease in the weight of fluid within the control container corresponds to a corresponding differential between the fluid pumped through the two tubes operating with the first pump. This error is determined and compensated for during therapy.

One apparatus and method for correcting a detected flow differential through the two tubes includes placing a closed-loop around each of the portions of the tubes operable with the first pump. A pressure relief valve is placed in each of these closed-looped lines. A valve is located downstream from each of the closed-loop lines. Thus if one tube is pumping more than the second tube, the valve corresponding to the higher flow tube can be closed, causing pressure in that closed-loop to build and correspondingly opening the relief valve. This enables the dialysate to idle around the closed-loop for a portion of time until the flow differential is corrected.

A further method of compensation also has the advantage of zeroing out any flow differential without the need to detect the differential beforehand. Here, line swapping flow paths are added upstream and downstream of the first path in combination with a valving arrangements that enable the flow of fresh and spent dialysate to switch back and forth in equal increments between the different tube segments operating with the first pump. Here, if any differential does exist through the two segments, the overall corresponding amount of fluid is made to be the same by switching the flows back and forth to cancel out the error. This is done without necessarily detecting the error.

In another embodiment, a third pump is added. Here the first pump drives only the fresh dialysate from the dialysate supply to the filter or diffusion membrane. The second pump as before pumps spent dialysate from the filter to the control container. The third pump is configured to pull spent dialysate from the control container and pump such spent dialysate to drain. The third pump is run to match flow and volume with the first pump, such that the amount of fluid delivered to the filter is the same amount of fluid removed from the control container. Here again, any increase or decrease in weight sensed by the weighing device occurring in the control bag corresponds to a net removal or addition of fluid into the patient. And a sensed rate of change corresponds to the rate of fluid removed or delivered to the patient.

In a further alternative embodiment, the control container is divided into fresh and spent portions. Additional fluid lines and valves are added, such that in one valve state the first or dual segment pump pumps fresh dialysate into and out of the fresh portion of the control container simultaneously. The second pump pumps fluid from the filter to a drain. This first valve state provides a calibration mode, which: (i) assures that the flow through the dual segments operable with the first pump is matched or (ii) enables a flow differential to be determined and corrected. In this first valve state, pump 20b is run at the same speed as pump one, enabling clearance but not ultrafiltration to occur. No corresponding ultrafiltration from the patient should take place because the corresponding increase in weight is not delivered to the control container.

In a second valve state, the dual segment first pump pumps fresh dialysate into the filter and at the same time removes spent dialysate from the spent portion of the control container and delivers same to drain. The second pump pumps fluid into the spent portion of the control container. This second valve state operates much like the embodiments described above, wherein flow to the filter and from the control container is matched theoretically, such that any increase or decrease in weight due to a mismatch in spent fluid pumped by the second pump into the spent portion of the control container corresponds to a net fluid loss or gain by the patient.

In a further alternative embodiment, the dual chamber control container is operated with three pumps. Here, the first pump drives fresh dialysate to the filter. The second pump pulls spent fluid from the filter. The third pump operates a loop that can either deliver fresh fluid to the control bag or remove spent fluid from the control bag. The dialysate pathways are valved such that: (i) the first pump can alternatively deliver fresh dialysate from the fresh portion of the control container to the filter; and (ii) such that the second pump can alternatively deliver spent dialysate from the filter to the control container.

In a first valve state, the first pump is configured to deliver fresh dialysate from the control container to the filter. The second pump is configured to drive spent fluid directly from the filter to drain. The third pump is configured to deliver fresh dialysate from the dialysate supply to the fresh portion of the control container. Here, the second pump is set to run at the same speed as the third pump, such that a gain in weight in the fresh compartment of the control container corresponds to an amount of ultrafiltrate that has been removed from the patient. Alternatively, a net loss in weight of fluid in the fresh portion of the control container corresponds to fluid having been added to filter and thus the patient.

In a second valve state, the first pump is configured to drive fresh dialysate directly from the supply to the filter. The second pump is configured to pump spent dialysate from the filter to the spent portion of the control container. The third pump is configured to pull spent dialysate from the spent portion of the control container and pump such spent dialysate to drain. Here, the first pump speed is set to equal the third pump speed. Thus any increase in weight in the control container corresponds to a like amount of ultrafiltrate being removed from the filter and the patient. On the other hand, any decrease in weight of fluid in the spent portion of the control container corresponds to a net amount of fluid being delivered to the dialyzer or the patient.

Various embodiments for the weighing device/control container configuration are also disclosed. In one embodiment, the weighing device includes a hook or similar mechanism from which the control container is hung. In another embodiment, the weighing device includes a platform onto which the control container is directly placed. Here, the control container is configured to be structurally rigid enough to support itself as well as the weight of dialysate pumped into the container. In a further alternative embodiment, a bin is placed on, attached to or formed integrally with the platform of the weighing device. The control container is placed in and supported by the bin. Here, the control container can be of a flexible material that can deform when placed in the bin.

In an embodiment, pressure regulators and/or pressure transducers are placed at the inlet of the dual segment or single segment pumping peristaltic pumps to help ensure that different peristaltic pumps pump the same flow, at equal speeds, when desired. Such regulators and transducers also help to ensure that the same pump operating dual pump segments pumps the same flow at equal speeds. The pressure regulators and/or transducers are alternatively placed in any combination either upstream or downstream of any of the peristaltic pumps in any of the embodiments described herein.

It is therefore an advantage of the examples discussed herein to provide a fluid control system for kidney failure treatments, which does not have to maintain constant the total volume of dialysate delivered and ultrafiltrate removed over an entire therapy.

It is another advantage of the examples discussed herein to provide a weight balancing fluid control system, which does not require complicated bag managing devices.

It is a further advantage of the examples discussed herein to provide a fluid control system for kidney failure treatments having improved ergonomics, such as one in which only a single bag has to be installed as opposed to multiple bags, easing removal and disposition of the single bag after therapy.

It is yet another advantage of the examples discussed herein to provide a weight balancing fluid control system having improved resolution.

It is yet a further advantage of the examples discussed herein to provide a weight balancing fluid control system that allows for spent dialysate to be discarded during therapy.

It is still another advantage of the examples discussed herein to provide a weight balancing fluid control system that minimizes post-treatment clean up.

It is still a further advantage of the examples discussed herein to provide a weight balancing fluid control system that is capable of using only a single weighing device.

Additional features and advantages are described herein, and will be apparent from, the following Detailed Description and the figures.

BRIEF DESCRIPTION OF THE FIGURES

FIG. 1 is a schematic illustration of one example of a kidney failure therapy weight balancing fluid control system in a first valve state.

FIG. 2 is a schematic illustration of the kidney failure therapy weight balancing fluid control system of FIG. 1 in a second valve state.

FIGS. 9 and 10 are schematic illustrations of a path sharing flow differentiation compensation apparatus and method in two different valve states, respectively.

FIG. 11 is a schematic illustration of a further example of a kidney failure therapy weight balancing fluid control system, which employs a third pump.

DETAILED DESCRIPTION

Figure 3A:
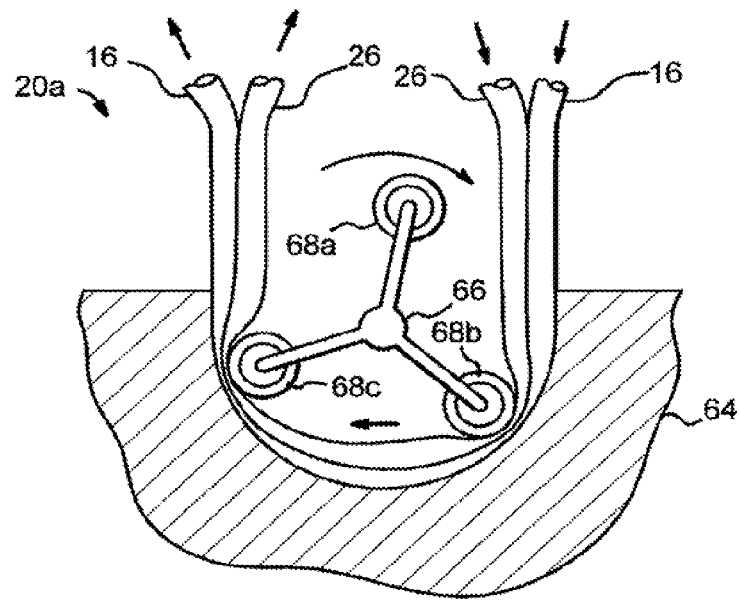
FIGS. 3A and 3B are elevation views of two embodiments for dual tubing peristaltic pumps used with the systems described herein.

The examples described herein are applicable to any medical fluid therapy system requiring the delivery to and/or removal of fluid from a patient to be monitored and/or controlled accurately. The systems are particularly well suited for the control of kidney failure therapies, such as all forms of hemodialysis ("HD"), hemofiltration ("HF"), hemodiafiltration ("HDF"), peritoneal dialysis ("PD," including continuous ambulatory peritoneal dialysis ("CAPD"), automated peritoneal dialysis ("APD"), tidal flow APD and continuous flow peritoneal dialysis ("CFPD") modalities). The systems may also be used in any type of continuous renal replacement therapy ("CRRT").

The examples below include a diffusion membrane or filter, such as a dialyzer, e.g., for HD or HDF, a hemofilter, e.g., for HF or a peritoneum, e.g., for PD. The drawings each show a to-filter and from-filter line, which is the case for HD. HDF includes an additional one or more fresh replacement fluid line (not shown) leading directly to the extracorporeal circuit, either upstream or downstream (or both) from the dialyzer. The additional one or more fresh replacement fluid line can be teed off of the to-filter line, for example.

Instead of the to-filter line, HF runs the same line to the extracorporeal circuit, either upstream or downstream (or both) from the hemofilter. HF uses the from-filter line as shown in the drawings.

In PD, the type of modality dictates the tubing configuration. CAPD and APD are batch-type systems, which typically require only a single line to the patient. Dialysate in CAPD and APD is typically delivered to the patient, allowed to dwell for a period, and then pumped from the patient and discarded to drain. Those cycles are then repeated a number of times. The to- and from-patient lines are teed together and valved appropriately, for example, so that dialysate can be delivered and removed at different times via the same single line and connection to and from the patient. CFPD typically uses a dual lumen catheter and thus requires the to-patient and from-patient (to-filter and from-filter) lines shown in the drawings.

Moreover, each of the systems described herein may be used in clinical or home settings. For example, the systems may be employed in an in-center HD machine, which runs virtually continuously throughout the day. Alternatively, the systems may be used in a home PD machine, which is typically run at night while the patient is sleeping.

The examples below include a dialysate (replacement fluid) supply, which for convenience is shown as a single bag of the fluid. Alternatively, multiple bags of dialysate supply are ganged together and used one after another. In such a case, the emptied supply bags can serve as drain or spent fluid bags. Further alternatively, each of the systems shown below can be used with an online source, such as one or more concentrate pump configured to combine one or more concentrate with water to form dialysate online. Online sources are used commonly with HD systems for example.

Although not illustrated, each of the systems shown and described herein can operate with an online or batch heater that heats the dialysate or replacement fluid to a desired temperature. The heater can be located upstream or downstream of the fresh supply pump for example. One or more air removal detector and device (e.g., air trap) is also provided for each of the systems in an embodiment. The air trap is in many instances located at or near the heater to capture air egression from the solution due to heating.

The flow schematics shown herein show the dialysate or replacement fluid portion of the kidney failure therapy device. HD, HF and HDF machines also include blood pumping systems, which are known in the art and need not be shown here. HD, HF and HDF also include dialysate proportioning systems, mentioned above, which are also known and need not be described here. The '534 patent, incorporated herein by reference, describes a proportioning system for example.

The dynamic weighing systems described herein can be used for a number of purposes. One purpose is to control ultrafiltration volume. The systems provide an accurate and relatively non-complex way of controlling and knowing how much ultrafiltrate has been removed from the patient. The systems ensure that the necessary amount of fluid is removed from the patient by the end of treatment.

Additionally, the systems can be used to control ultrafiltration ("UF") rate. The '534 patent, incorporated herein by reference, describes UF profiling, which enables the rate at which fluid is removed from the patient to vary desirably over the course of treatment. Because the weighing systems are dynamic, they allow information to be determined on a real time basis. For example, the systems can determine that one hundred milliliters ("ml") of fluid have been removed from the patient over the past minute, yielding a UF rate of 100 ml/min. That actual rate can then be compared to a desired rate set according to a prescribed UF profile, so that the pumps can be adjusted if needed to make the actual rate equal the desired rate.

The systems described herein are also provided in an enclosure (not illustrated for convenience) The enclosures will vary depending on the type of treatment, whether the treatment is in-center or a home treatment, and whether the dialysate/replacement fluid supply is a batch-type (e.g., bagged) or online. The in-center, online enclosures tend to be bigger and more robust due to the additional dialysate producing equipment and the frequency of use of such machines. Home therapy enclosures are desirably smaller and built so that the machines can be moved about ones home or for travel.

Referring now to the drawings and the particular to FIGS. 1, 2, 3A to 3B, one example of a dynamic weight or gravimetric balancing system is illustrated by the system 10. System 10 is shown in a first valve state in FIG. 1 and in a second valve state in FIG. 2. As shown in FIGS. 1 and 2 (and as maintained throughout this application, as shown in the key below filter 18), valves that are currently open are shown unbolded or uncolored, while valves that are currently closed are shown bolded or colored. System 10 includes a dialysate or replacement fluid supply 12, which can be any of the types described above. As used herein, the term "dialysate" is meant to cover any of the batch or online fluids prepared in any of the treatments discussed above, including dialysate four HD and HDF. The term also encompasses any dialysate made for any batch or continues type of PD system (dialysate for PD includes glucose in a high concentration). Further, the term dialysate covers replacement fluid used in HF and HDF.

System 10 also includes a drain bag 14, which can be a single drain bag, a plurality of drain bags, a large drain container. System 10 also includes a house drain 24, which can any type of a toilet or any type of drain installed in a hospital, home or clinic. A fresh dialysate line 16 is connected fluidly to dialysate supply 12 and the inlet of filter 18. Filter or diffusion membrane 18 can be any of the types discussed above. Dialysate supply line 16 is also coupled operably to a first pump 20a, which in an embodiment is a peristaltic pump. Peristaltic pump 20a is discussed in more detail below in connection with FIGS. 3A and 3B.

A drain line 22 is connected fluidly between drain bag 14 and/or house drain 24. A first spent dialysate line 26 is connected fluidly to a control container 30 and drain line 22. First spent dialysate line 26 is also coupled operably (along with fresh supply line 16) to first peristaltic pump 20a. A second spent dialysate line 28 is connected fluidly to the outlet of filter or diffusion membrane 18 and control bag 30. Second spent dialysate line 28 is coupled operably to peristaltic pump 20b. First and second valves 32 and 34 as illustrated are configured to selectably occlude drain line 22 at positions located on either side of the fluid connection between first spent dialysate line 26 and drain line 22.

Figure 20:
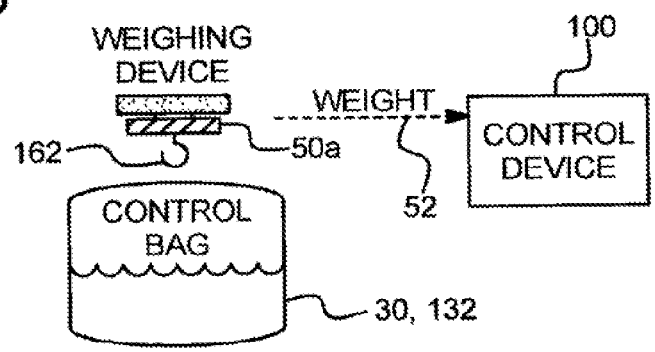
FIGS. 20 to 22 are schematic illustrations of different embodiments for weighing device/control container combinations used with the systems described herein.
Figure 21:
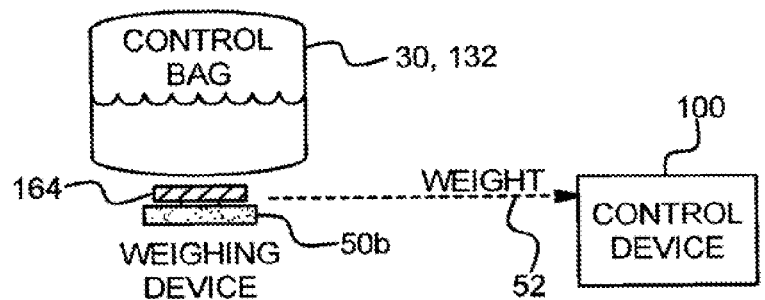
Figure 22:
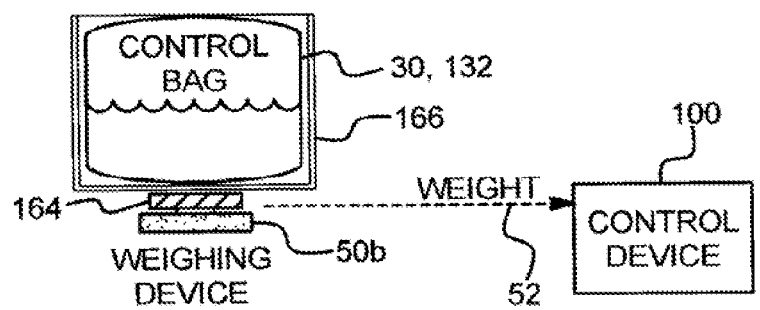

Control bag 30 is coupled operably to a weighing device or scale 50. Various combinations of control bag 30 and weighing device 50 are shown and described below in connection with FIGS. 20 to 22. Any of the embodiments shown below in connection with FIGS. 20 to 22 is applicable to any of the systems described herein, including system 10.

Weighing device 50 sends an electronic signal 52, such as a zero to five VDC or four to twenty mA signal (analog in one embodiment) to a control device 100. Control device 100 can be any suitable type of logic implementor, such as one containing any one or more of a processor, a random access memory ("RAM"), a read-only memory ("ROM") or an application specific integrated circuit ("ASIC"). In an embodiment, control device 100 is a subcontroller or delegate printed circuit board ("PCB"), which communicates with one or more supervisory, master control or motherboard. For example, control device 100 can be a printed circuit board, which controls certain related functions, such as UF control, dialysate proportioning, dialysate pressure control, dialysate temperature control, and other related dialysate parameters. The use of subcontrollers in combination with one or more motherboard is discussed in the '534 patent, incorporated herein by reference.

Besides signal 52, control device 100 receives and generates additional signals, which may be of any suitable type including those listed above for signal 52. Any of the signals generated and/or received by control device 100 may be analog or digital. For example, control device 100 also receives pressure signals 54a and 54b from pressure transducers 56a and 56b, respectively. Control device 100 further generates and sends signals 58a and 58b to pumps 20a and 20b. In an embodiment, signals 58a and 58b are variable current signals that control the speed of pumps 20a and 20b. Signals 58a and 58b are alternatively pulsed voltage or transistor-transistor logic ("TTL") type signals that are sent to a local controller at pumps 20a and 20b. The local pump controllers convert the digitized signals into motor currents that control the speed of pumps 20a and 20b.

Control device 100 also sends signals 62a and 62b to valves 32 and 34. Valves 32 and 34 in an embodiment are normally open or normally closed solenoid valves. Signals 62 and 62b electronically and automatically control whether any particular valve is open or closed at any particular time. Control device 100 in an embodiment maintains software that sequences the valves, such as valves 32 and 34 at appropriate times. Control device 100 also maintains software that compares the value at any given time for signal 52 from weighing device 50 with a preset or desired value, which determines whether enough fluid is maintained within control bag 30 or whether UF rate is proper, and thus whether to speed up or slow down one or both of pumps 20a and 20b.

As illustrated, peristaltic pump 20a has a common head that drives fresh dialysate from supply 12, through fresh supply line 16 to the input of filter 18, while at the same time pulling the spent dialysate from control bag 30, through the first spent dialysate line 26, to drain line 22, and thereafter to either drain bag 14 or house drain 24.

Figure 3B:
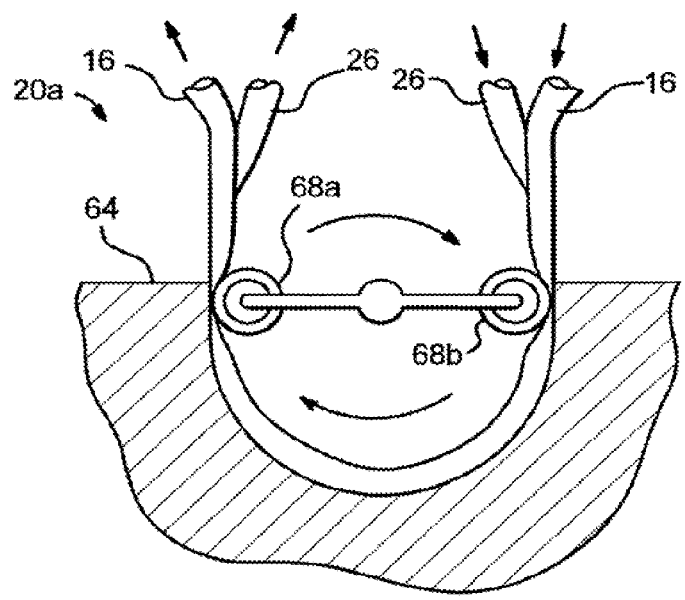

Referring additionally to FIGS. 3A and 3B, which show enlarged views of two embodiments for peristaltic pump 20a driving two pumping segments of tubes 16 and 26, matching the flow through each segment 16 and 26 theoretically. In each case, peristaltic pump 20a includes a race 64 and a roller spindle 66 having three drive rollers 68a to 68c, for example, in FIG. 3A, and two drive rollers 68a and 68b in FIG. 3B. Other peristaltic pump configurations (e.g., more or less rollers, cylindrical versus tapered rollers, linear rollers) may be employed alternatively. Peristaltic pumps, such as pump 20a, are used typically to pump clean or sterile fluids, such as dialysate or replacement fluid, because the pump hardware does not contact and thus contaminate the fluid. The only part of the pump in contact with the dialysate/replacement fluid is the interior of the tube segments of lines 16 and 26 contacting race 64, which are cleaned and sterilized before therapy. Also, because peristaltic pumps include no moving parts in contact with the dialysate/replacement fluid, the pumps are relatively inexpensive. Peristaltic pumps also lack the valves, seals and glands used in other types of pumps, which makes pump 20a for example comparatively inexpensive and easy to maintain.

The primary difference in pump 20a of FIG. 3A is that in FIG. 3A, the rollers pinch tubes 16 and 26 together against race 64. Here, tube 16 is filled between tube 26 and race 64. In pump 20a of FIG. 3B, on the other hand, tube 16 lies in front of tube 26. Here, length of rollers 68a and 68b extends far enough so that they can contact both tubes 16 and 26, which are placed directly adjacent to each other in one embodiment.

In the operation of system 10 of FIGS. 1 and 2, control container 30 contains a fixed volume of dialysate at the start of treatment. As discussed above, weighing device 50 weighs control container 30 constantly and sends a constant signal 52 representing the weight of dialysate within control bag 30 to control device 100. Pump 20b pumps spent dialysate from filter or diffusion membrane 18 into control container 30. Simultaneously, pump 20a drives fresh fluid from supply 12 into filter 18. Pump 20a also simultaneously pumps spent fluid from control container 30 to either drain bag 14 or house drain 24.

In an embodiment, the pressure of dialysate in lines 16 and 26 upstream or at the inlet side of pump 20a is at or close to atmospheric. Differences in pressure of dialysate in lines 16 and 26 are measured or read by pressure transducers 56a and 56b which send corresponding signals 54a and 54b to control device 100 (see also FIGS. 23 and 24). Pressure differences of an elevated magnitude may indicate a mechanical error, for example, causing flow through lines 16 and 26 to not be matched.

Assuming pump 20a pumps the same flow through lines 16 and 26, the volume of fresh dialysate sent to filter 18 is or should be at least substantially equal to the volume of spent fluid that is removed from control container 30. If no ultrafiltration is desired, for example if it is desired to run a therapy or a portion of therapy in which fluid is not to be removed from the patient, then pump 20b is adjusted so that the weight of spent dialysate maintained within control container 30 is constant or unchanging. That is, the amount or rate of fluid being delivered to filter 18 is the same as the amount or rate of fluid that is being removed from filter 18, which is the same as the amount or weight of fluid that is being pumped to drain 14 or 24.

If ultrafiltration is desired, that is if it is desired to run system 10 to produce a resulting net removal of fluid from the patient, then control device 100 adjusts the speed of pump 20b such that spent dialysate pulled from filter 18 accumulates within control container 30 at a predetermined rate. The faster pump 20b is run with respect to the speed of pump 20a, the faster the spent dialysate fills control container 30, and thus the faster that ultra filtrate is removed from the patient.

System 10 provides a negative feedback loop, with control container 30 measuring the error or imbalance between the flow of fresh dialysate and spent dialysate. Because system 10 balances the flow of fresh and spent dialysate via the measurement of error, the need to preserve or maintain the total volume of each of these fluid flows is not necessary. This arrangement allows for the continuous disposal of spent dialysate to drain 14 or 24 (via the configuration of valves 32 or 34). In older systems, spent fluid would have to be accumulated, e.g., in drain bag 14, for the purpose of comparing (e.g., for controlling UF) the amount of spent dialysate in drain bag 14 with the amount of fresh dialysate delivered from supply 12. In system 10, such overall comparison is not necessary. This eliminates problems inherent in such weighing systems, such as inherent inaccuracy, misplacement or movement of bags during therapy, and other problems listed above.

It should be appreciated that control device 100 of system 10 can readily and accurately calculate the total volume of fluid removed from the patient by dividing the weight of spent dialysate gained within control container 30 over the course of treatment by the density of spent dialysate. The amount or volume of fluid delivered to filter 18 or to drain 14 or 24, which is less important to monitor than the amount of UF removed, can be at least approximated by multiplying the number of revolutions made by the head of pump 20a by an average volume of fluid pumped per revolution. If needed, system 10 can employ flow accumulating devices that monitor the flow and/or amount of fluid flowing through lines 16 and 22 and send a signal to control device 100 for readout and therapy record keeping purposes.

The matched rate-based system 10 lends itself readily to the above-described UF profiling. Keeping the rate of pump 20a constant, control device 100 of system 10 can vary the speed of pump 20b according to a stored UF profile to vary the rate of ultrafiltration desirably over time and, for example, remove more UF over the first half of therapy than over the second half. In this manner, system 10 can control the speed of pumps 20a and 20b according to any suitably desirable UF profile.

The assumption of equal flow through fresh supply line 16 and first spent dialysate line 26 via the pumping of pump 20a is not necessarily or absolutely correct. The manufacturing tolerances of the tubes and/or inconsistencies in the race 64 of pump 20a (as seen in FIG. 3) could cause flow through one of the lines 16 or 26 to be greater or less than flow through the other line. Described below are various apparatuses and methods for detecting and/or correcting for differences between the flow through the segments of lines 16 and 26 operating with pump 20a. A first apparatus and method is discussed in connection with system 110 of FIGS. 4 and 5.

Figure 4:
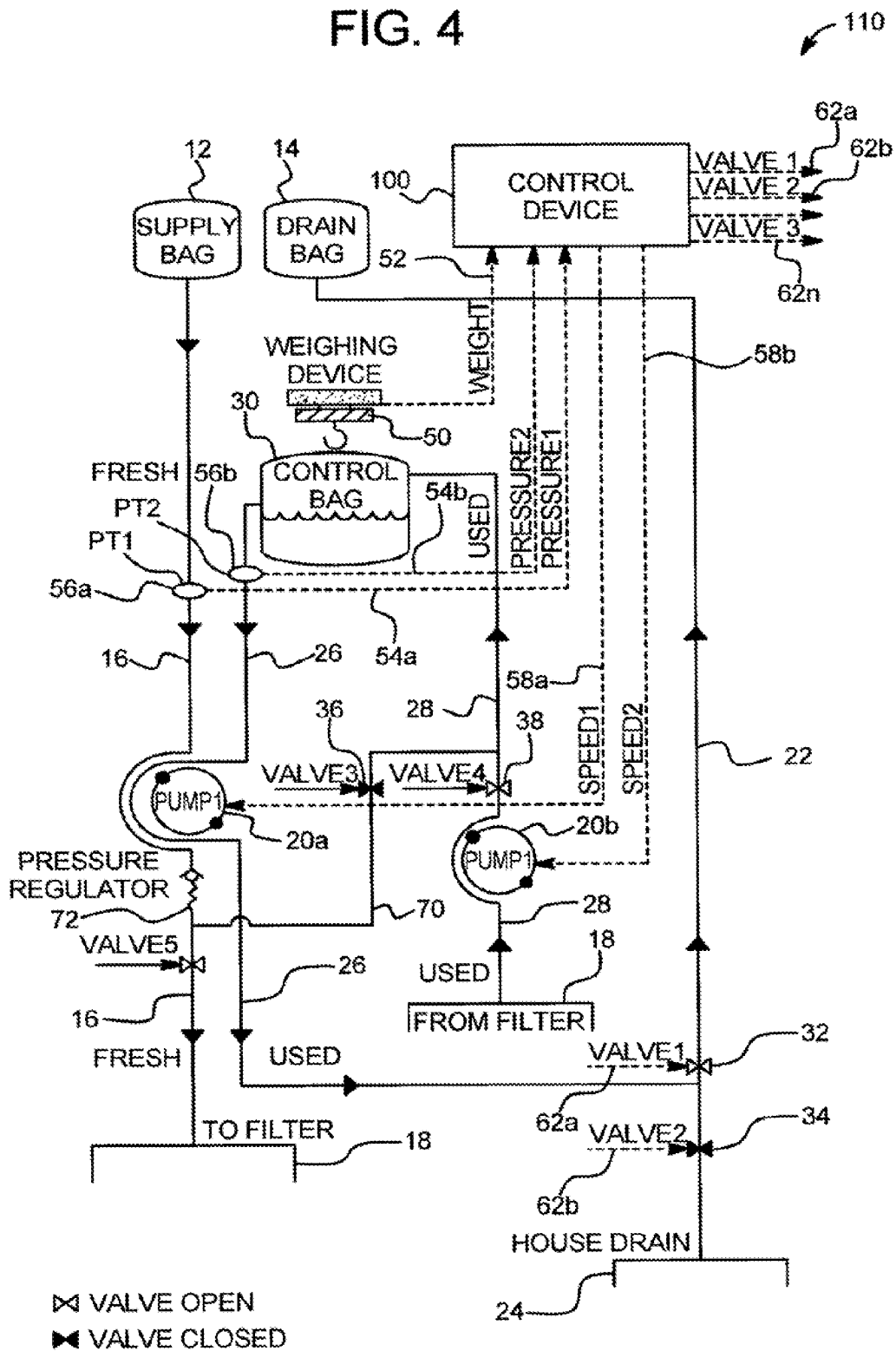
FIG. 4 is a schematic illustration of another example of a kidney failure therapy weight balancing fluid control system in a first valve state.
Figure 5:
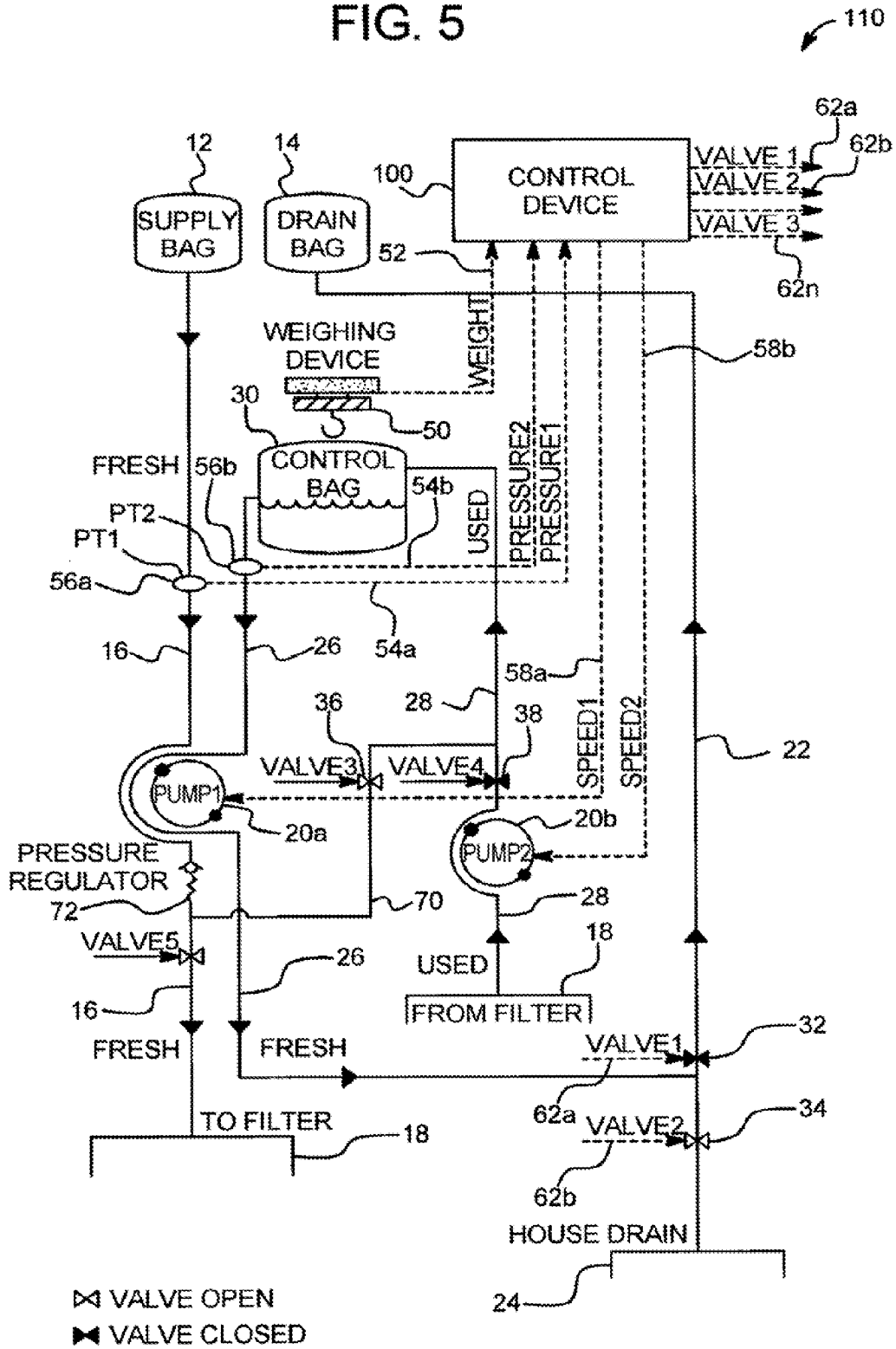
FIG. 5 is a schematic illustration of the kidney failure therapy weight balancing fluid control system of FIG. 4 in a second valve state.

Referring now to FIGS. 4 and 5, alternative system 110 is illustrated. System 110 includes many of the same components described above for system 10, such as supply 12, drain bag 14, fresh supply line 16, filter 18, peristaltic pumps 20a and 20b, drain line 22, house drain 24, first spent dialysate line 26, second spent dialysate 28, control bag 30, solenoid valves 32 and 34, weighing device 50, signal 52 from weighing device 50 to control device 100, signals 54a and 54b from respective pressure transducers 56a and 56b to control device 100, pump speed output signals 58a and 58b to pumps 20a and 20b, and solenoid output signals 62a to 62n to control solenoid valves, such as valves 32 and 34. Segments of lines 16 and 26 are again driven simultaneously by pump 20a. A segment of line 28 is again driven by pump 20b.

A pressure regulator 72 is placed in supply line 16, downstream from pump 20a. Pressure regulator 72 sets a pressure upstream of regulator 72, between the regulator and pump 20a. The pushback by regulator 72 helps the output of pump 20a to be more steady, e.g., reduced pressure and/or flow fluctuations. The regulation of upstream pressure tends to make the output through the segment of line 16 operating with pump 20a be more closely matched to the pressure and volumetric characteristics of segment 26 operating with pump 20a. The pumping regime is thereby more volumetrically accurate. Although not illustrated, a regulator 72 can be additionally or alternatively positioned in line 26 downstream from pump 20a. Further, any of the pumps 20a, 20b, 20c, etc., described herein can operate with a downstream regulator 72.

The primary difference between system 110 and system 10 is that a bypass line 70 is added to enable fluid communication between fresh supply line 16 and second spent dialysate line 28. A third valve 36 is positioned to open or occlude bypass line 70. A fourth valve 38 is positioned to open or occlude line 28 downstream of pump 20b. A fifth valve 40 is positioned to open or occlude fresh supply line 16, at a point prior to the connection of line 16 and filter 18.

System 110 when valve 36 is closed and valve 38 is open as seen in FIG. 4 behaves the same as system 10 described previously. That is, pump 20a matches fresh dialysate pumped to filter 18 with spent dialysate pulled from control container 30. Control device 100 controls the rate of ultrafiltration, if any, by varying the speed of pump 20b as needed. It should be noted that in this valve state, valve 40 is opened to enable fresh dialysate to flow from supply 12 to filter or diffusion membrane 18.

When the state of the valves in FIG. 4 is reversed, as shown in FIG. 5, system 110 closes valves 38 and 40 and opens valve 36 to stop dialysate flow to and from filter 18. In this state, filter 18 is bypassed. Pump 20b is stopped. Pump 20a pumps dialysate to container 30 from supply 12 and dialysate from container 30 via line 26 simultaneously. Weighing device 50 in combination with control device 100 attempt to detect any gain or loss of fluid within control container 30. If the flow through fresh supply line 16 is greater than the flow through first spent dialysate line 26, then fluid accumulates in control container 30. A corresponding signal 52 is detected by control device 100, which adjusts pump 20b accordingly when the valves are reverse to the therapy state of FIG. 4. Conversely if flow through first spent dialysate line 26 is greater than the flow through fresh supply line 16, then the amount of fluid in control container 30 will decrease over time, causing a corresponding drop in weight would be measured and delivered to control device 100. Diagnostic valve state of FIG. 5 it should be appreciated detects differences in flow through the segments of lines 16 and 26 communicating with pump 20a.

In either case, the difference in flow through the lines 16 and 26 can be determined and compensated for by controlling the speed of pump 20b once therapy is resumed. For example, if fresh dialysate is being pumped to filter 18 at a rate X faster than fluid is being pulled from control container 30, then the speed of pump 20b can be increased by rate X to produce the desired rate of UF removal. On the other hand, if fluid is being pulled from control container 30 at a rate Y faster then fluid is being delivered to filter 18, then the speed of pump 20b can be reduced by rate Y to achieve the desired rate of UF removal.

In an embodiment, control device 100 of system 110 is configured to periodically switch from the normal operating valve state of FIG. 4 to the diagnostic bypass valve state of FIG. 5. Each time, control device 100 recalculates the delta rate of dialysate that pump 20a is pumping through lines 16 and 26 and adjusts pump 20b accordingly.

System 110 can also detect a potentially catastrophic difference between the rates of fluids pumped through lines 16 and 26 by pump 20a. For example, if the error between the two rates is too large, control container 30 may not have enough capacity to compensate for the error over the course of treatment. For example, if the rate of fluid being removed from controlled container 30 is too slow, container 30 may overflow by the end of therapy. System 110 is configured to detect such a condition, send an error message to the patient or operator, and potentially shut down the pumping of the system.

Figure 6:
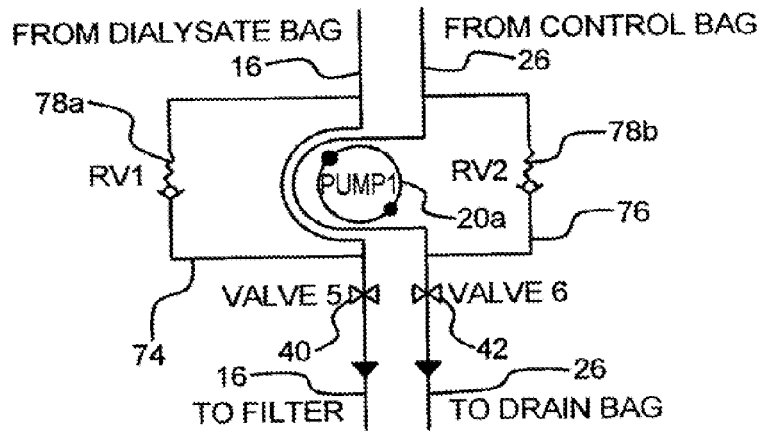
FIGS. 6 to 8 are schematic illustrations of a closed loop flow differentiation compensation apparatus and method in three different valve states, respectively.
Figure 7:
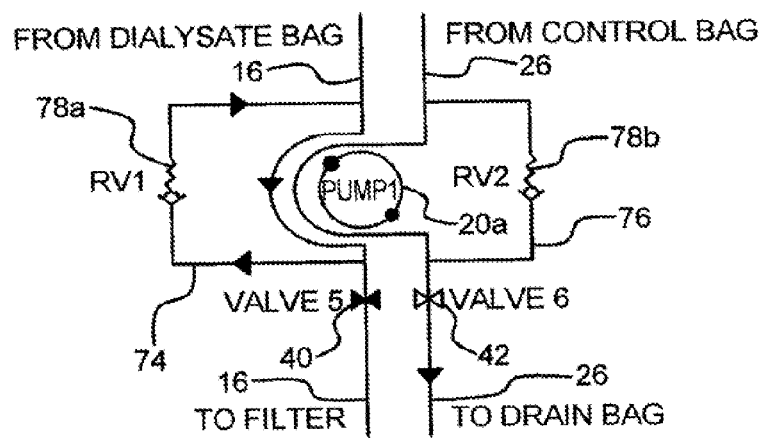
Figure 8:
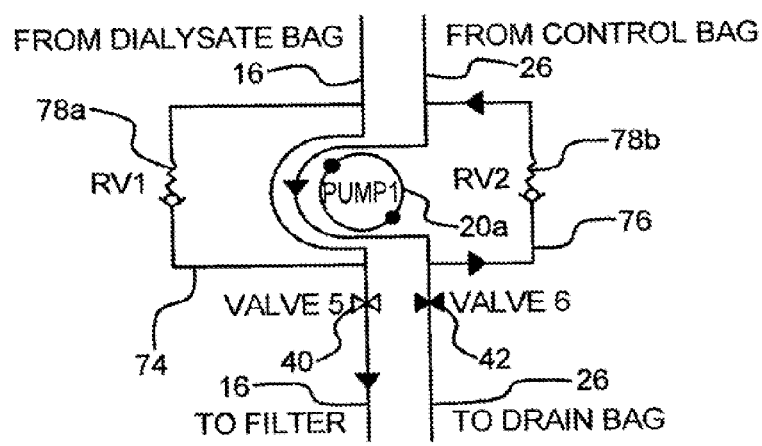

An apparatus and method for compensating a difference in flow between fresh supply line 16 and first spent dialysate line 26 via the pumping of single pump 20a is illustrated in connection with FIGS. 6 to 8. FIGS. 6 to 8 show a portion of an overall system, which can be any suitable overall system described herein, such as system 10.

In the system employing the arrangement of FIGS. 6 to 8, valves 40 and 42 are added to lines 16 and 26, respectively, downstream of pump 20a. Closed loop producing or loop-closing lines 74 and 76 are placed in fluid communication with lines 16 and 26, respectively, producing in each line a closed fluid loop around pump 20a. Each closed loop producing line 74 and 76 has a corresponding relief valve 78a and 78b. The configuration in FIGS. 6 to 8 enables one of the lines 16 or 26 to desirably stop driving fluid to its therapeutic destination. FIG. 6 shows the normal operating state when pump 20a pumps fluid through both lines 16 and 26.

Closing valve 40, as seen in FIG. 7, causes the pressure in line 16 upstream of valve 40 to increase. Eventually, when the pressure reaches a certain point, relief valve 78a opens causing pump 20a to pump fresh dialysate back through closed loop line 74 to the upstream side of pump 20a. This closed loop stops the flow of fresh dialysate to filter 18. In the meantime, pump 20a continues to pump spent dialysate from control container 30, through line 26, and through open valve 42 to drain 14 or 24. This state is shown in FIG. 7.

FIG. 8 shows the reversed state with valve 42 closed and valve 40 open. Here, pressure builds in the closed loop line 76 to a point at which pressure relief valve 78b opens, enabling fluid to flow through closed loop line 76, creating a closed loop around pump 20a in line 26, and stopping dialysate flow from control container 30 to drain bag 18. At the same time, pump 20a pumps fluid from supply 12 to filter 18.

The apparatus and method of FIGS. 6 to 8 is a flow compensation apparatus, which can be used in combination with any type of error detecting scheme to compensate for a detected error. For example, the apparatus and method of FIGS. 6 to 8 can be used for compensation in system 110 of FIGS. 4 and 5 instead of adjusting the rate of pump 20b. Alternatively, the compensation apparatus and method of FIGS. 6 to 8 could be used with any error determining scheme for detecting differences in flow in lines 16 and 26 during a calibration mode. During therapy, control device 100 closes either valve 40 or 42 temporarily for as long or as many times as needed to maintain the weight in control container 30 constant or to have the weight increase according to a desired UF rate or UF profile.

Referring now to FIGS. 9 and 10, another apparatus and method for compensating between a difference of flow in lines 16 and 26 is illustrated. FIGS. 9 and 10 again show a portion of an overall system, which can be any suitable overall system described herein, such as system 10. As will be appreciated, the compensation apparatus and method of FIGS. 9 and 10 is desirable in one aspect because it automatically compensates for flow differences caused by tubing and pump race inconsistencies without having to detect such differences. The apparatus and method of FIGS. 9 and 10 can also be incorporated as desired into the overall systems described herein The apparatus and method of FIGS. 9 and 10 includes a pair of line swapping flow paths 48a and 48b located downstream of pump 20a. A pair of line swapping flow paths 88a and 88b are also provided upstream of pump 20a. Each of the line swapping flow paths establishes a valved fluid communication between fresh supply line 16 and first spent dialysate line 26.

As seen in FIGS. 9 and 10, line swapping flow path 48a operates with occluding solenoid 44, while flow path 48b operates with occluding solenoid 46. Valves 40 and 42 operate to occlude or not occlude lines 16 and 26 downstream of pump 20a, respectively. Valves 80, 82, 84 and 86 operate to occlude or not occlude line 16, line 26, line 88a and line 88b, respectively.

The valving and line swapping arrangement of FIGS. 9 and 10 enables fresh dialysate to flow selectively through either of the segments of lines 16 and 26 operating with pump 20a. The configuration likewise enables spent dialysate from control container 30 to be pumped alternatingly through either segment of lines 16 and 26 operable with pump 20a.

In FIG. 9, fluid flows from supply 12 (see, e.g., system 10, FIGS. 1 and 2), past valve 80, line 16, the segment of line 16 contacting pump 20a, and past valve 40 to filter 18. Simultaneously, spent dialysate is pumped from control container 30 through line 26, past valve 82, through the segment of line 26 contacting pump 20a, and past valve 42 to drain bag 14 or house drain 24.

In FIG. 10, the valve states are reversed such that pump 20b pumps fresh dialysate from supply 12, through line swapping flow path 88b, past valve 86, through the segment of line 26 in contact with line 20b, through line swapping flow path 48a, past valve 44, and back into line 16 to filter 18. Simultaneously, pump 20b pumps spent dialysate from control bag 30, through line swapping flow path 88a, past valve 84, through the segment of line 16 in contact with pump 20b, through line swapping flow path 48b, past valve 46 and back into line 26 to drain bag 14 or house drain 24.

The valves of FIGS. 9 and 10 are switched so that the flow of fresh dialysate to filter 18 matches or at least substantially matches the flow of spent dialysate from control bag 30 to one of the drains. The paths may be switched so each different fluid is pumped half the time through each segment of lines 16 and 26 operating with pump 20a. Alternatively, the system of FIGS. 9 and 10 operates with a flow differential detection method such that the valves are maintained in one state until it is determined that a switch needs to be made, after which the valves switch until the flow differential is compensated or another switch needs to be made, and so on.

Referring now to FIG. 11, another apparatus and method of compensating for differences of dialysate flow through segments 16 and 26 operating with pump 20a is illustrated by system 120. Here, line 26 is removed from pump 20a and is instead made to operate with a third pump 20c, which receives a pumping speed signal 58c from control device 100. Bypass line 70 and valves 36, 38 and 40 are provided as described above in connection with system 110 of FIG. 4. FIG. 11 shows a normal therapy valve state with valves 38 and 48 open and valve 36 closed, allowing dialysate to flow to and from filter 18.

In a second valve state (not shown), system 120 closes valves 38 and 40, opens valve 36 and uses bypass line 70 to determine any differential between the dialysate flow pumped by pumps 20a and 20c through lines 16 and 26, respectively. Once any error is determined, the valves are switched back to the therapy valve state, and control device 100 sets the speed of pumps 20a to 20c accordingly to match the flow of fresh and spent dialysate fluid through lines 16 and 26 during therapy. During therapy, control device 100 adjusts pump 20b to remove UF, if at all, from the patient according to a predetermined rate or UF profile. Control device 100 may be configured to intermittently return to the second calibration state intermittently or as needed to redetermine any error in flow between pumps 20a and 20c.

Referring now to FIGS. 12 to 15, a system including another apparatus and method for compensating between the differences in flow the dual tubing segments operating with pump 20a is illustrated by system 130. System 130 includes many of the components already described herein, such as, supply 12, drain 14, 24, lines 16 and 22, filter 18, pumps 20a and 20b, weighing device 50, etc. For ease of illustration, control device 100 is not shown, nor are the signal lines leading to control device 100 from weighing device 50, the output signal lines to pumps 20a and 20b, or the output signal lines to the valves shown in FIGS. 12 to 15. System 130 includes all such structures and can include pressure transducer(s), pressure regulator(s) and/or relief valve(s) in one or more suitable places as necessary.

One primary difference in system 130 is that a different control container 132 is employed. Here, control container 132 is divided into fresh and spent dialysate portions 134 and 136. That is, fresh dialysate is pumped into and out of fresh portion 134 of container 132, while spent dialysate is pumped into and out of spent portion 136 of container 132. One advantage of system 130 is that control bag 132 precludes mixing of spent and fresh dialysate (which is more important when supply 12 is bagged, sterile dialysate or replacement fluid versus dialysate made online).

In system 130, pump 20a pumps fresh dialysate from supply 12 through line 16 to the filter or diffusion membrane 18 as before. Here, however, pump 20a is also configured to pump either fresh dialysate through a loop 126 to the inlet of fresh portion 134 of container 132 or spent dialysate from the outlet of spent portion 136 of container 132 to drain. Loop 126 is accordingly connected fluidly to the inlet of fresh portion 134 and the outlet of spent portion 136 of container 132.

System 130 includes a number of additional flow paths. A fresh bypass supply line 138 is connected fluidly to line 16 (between supply 12 and pump 20a) and loop 126 (upstream of pump 20a). A fresh bypass return line 128 is connected fluidly to line 16 (between supply 12 and pump 20a) and to the outlet of fresh portion 134 of control container 132. A spent bypass supply line 142 is connected fluidly to drain line 22 (downstream of pump 20b) and to the inlet of spent portion 136 of control bag 132. A bypass line 140 is also connected between loop 126 (downstream of pump 20a) and drain line 22 (downstream of pump 20b).

System 130 also includes a number of additional valves. A valve 144 is coupled operably to fresh supply line 16 upstream of pump 20a. A valve 146 is coupled operably to loop 126 prior to the inlet of fresh portion 134 of bag 132. A valve 148 is coupled operably to fresh dialysate return line 128. A valve 150 is coupled operably to bypass line 140. A valve 152 is coupled operably to spent bypass supply line 142. A valve 154 is coupled operably to fresh bypass supply line 138. A valve 156 is coupled operably to dialysate line 22 downstream of pump 20b. A valve 158 is coupled operably to loop 126 upstream of pump 20a.

Figure 12:
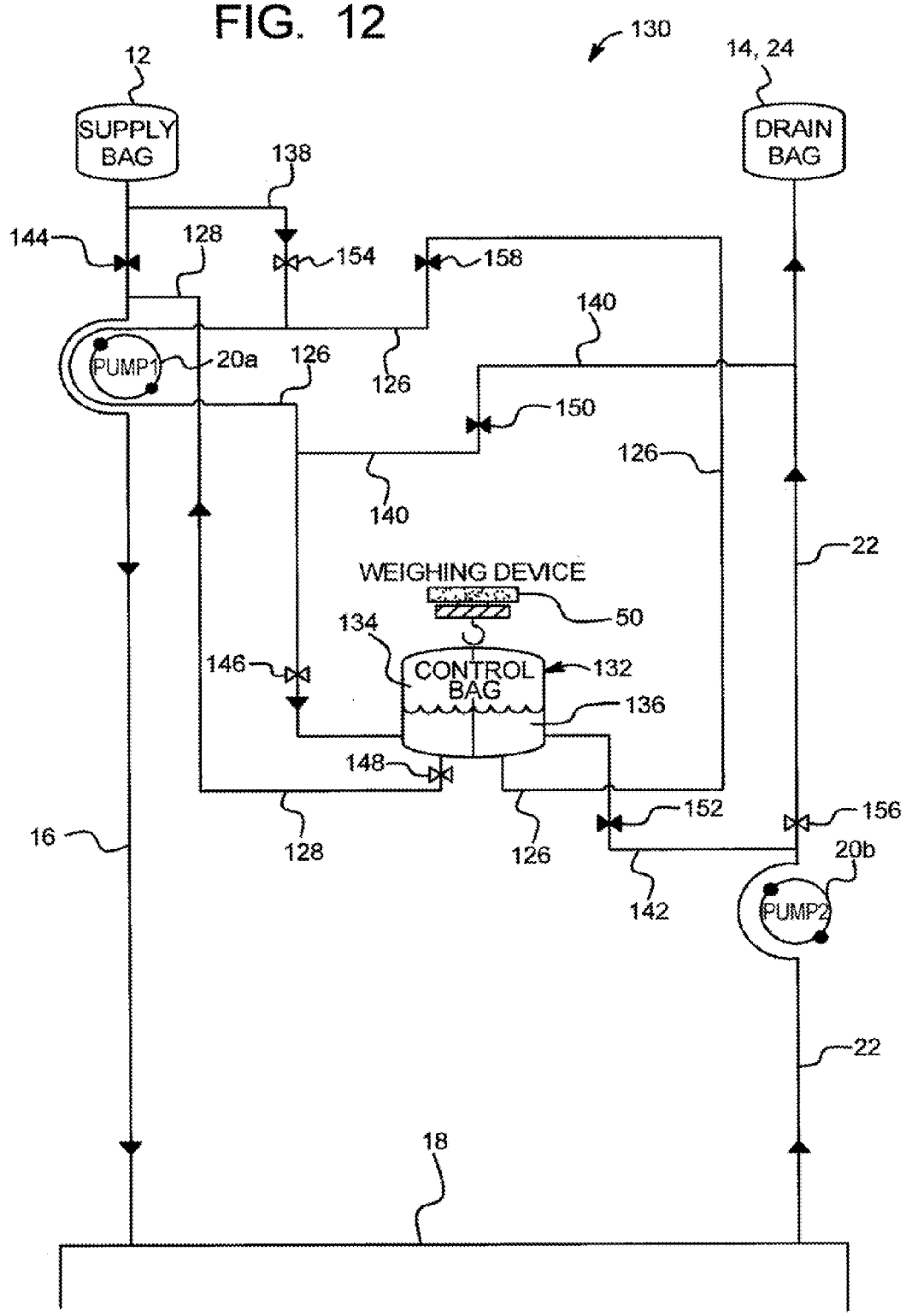
FIG. 12 is a schematic illustration of yet another example of a kidney failure therapy weight balancing fluid control system in a first valve state, which has a control container with separated fresh and spent portions.
Figure 13:
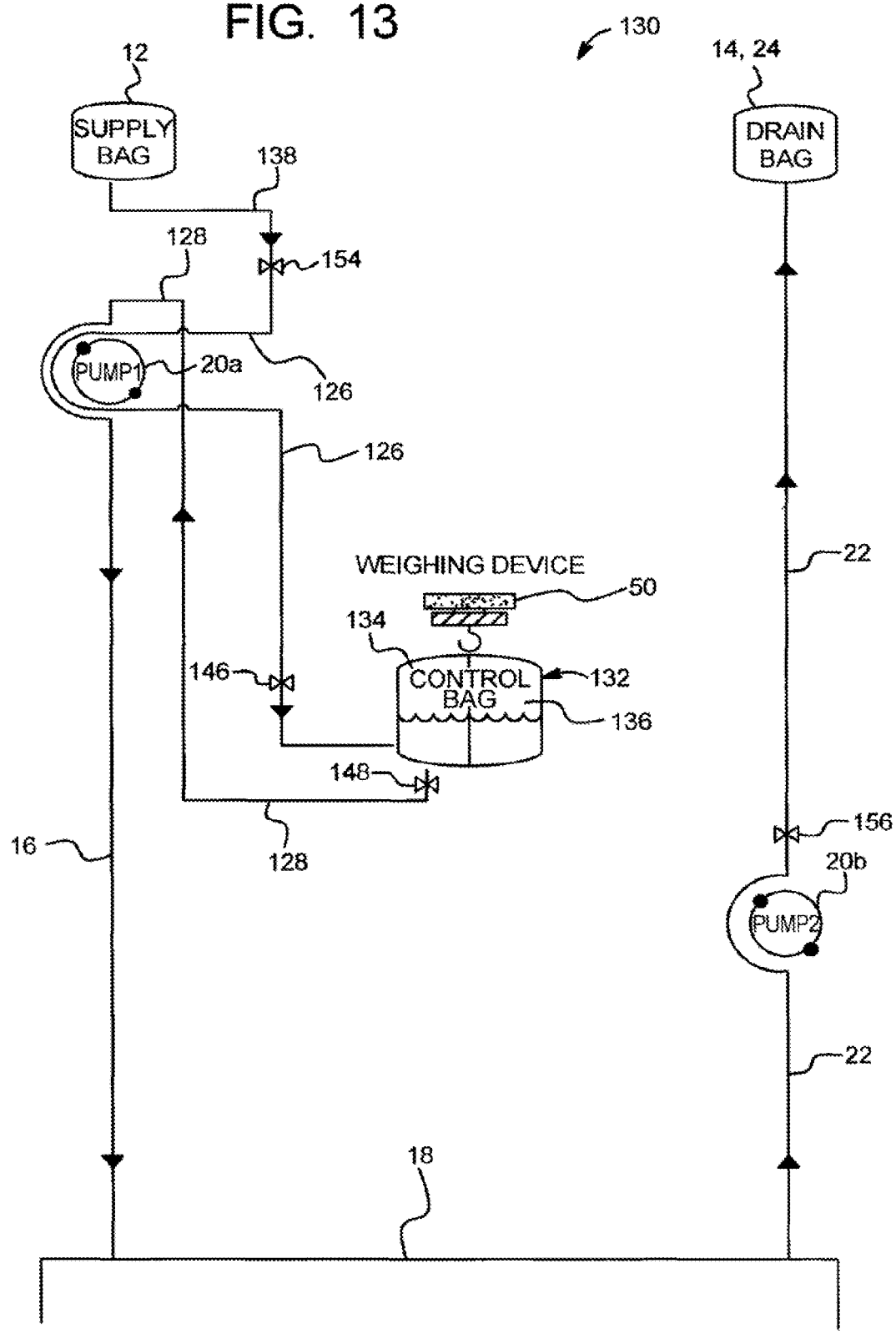
FIG. 13 is a schematic illustration of the kidney failure therapy weight balancing fluid control system of FIG. 12 in the first valve state with closed-off sections of the flow path eliminated for clarity.

FIGS. 12 and 13 show system 130 in a first valve state. Here, loop 126 of double segment pump 20a is used to pump fresh dialysate into fresh chamber 134 of control container 132. For purposes of illustration, sections of the fluid loop that are not used in the valve state of FIG. 12 are removed in FIG. 13. In FIGS. 12 and 13, valves 146, 148, 154 and 156 are opened, while all other valves are closed. As seen most readily in FIG. 13, pump 20a pumps fresh fluid from supply 12, through line 138, past valve 154, through the portion of loop 126 shown in FIG. 13, through the inner tubing segment operating with pump 20a, past valve 146 and into fresh portion 134 of control bag 132. From control bag 132, pump 20a pumps fresh dialysate past valve 148, through fresh bypass return line 128, through the outer tubing segment operating with pump 20a, to the inlet of filter or diffusion membrane 18. At the same time, pump 20b pumps spent dialysate from filter or diffusion membrane 18, past valve 156, through line 22, to drain bag 14 or house drain 24.

Figure 14:
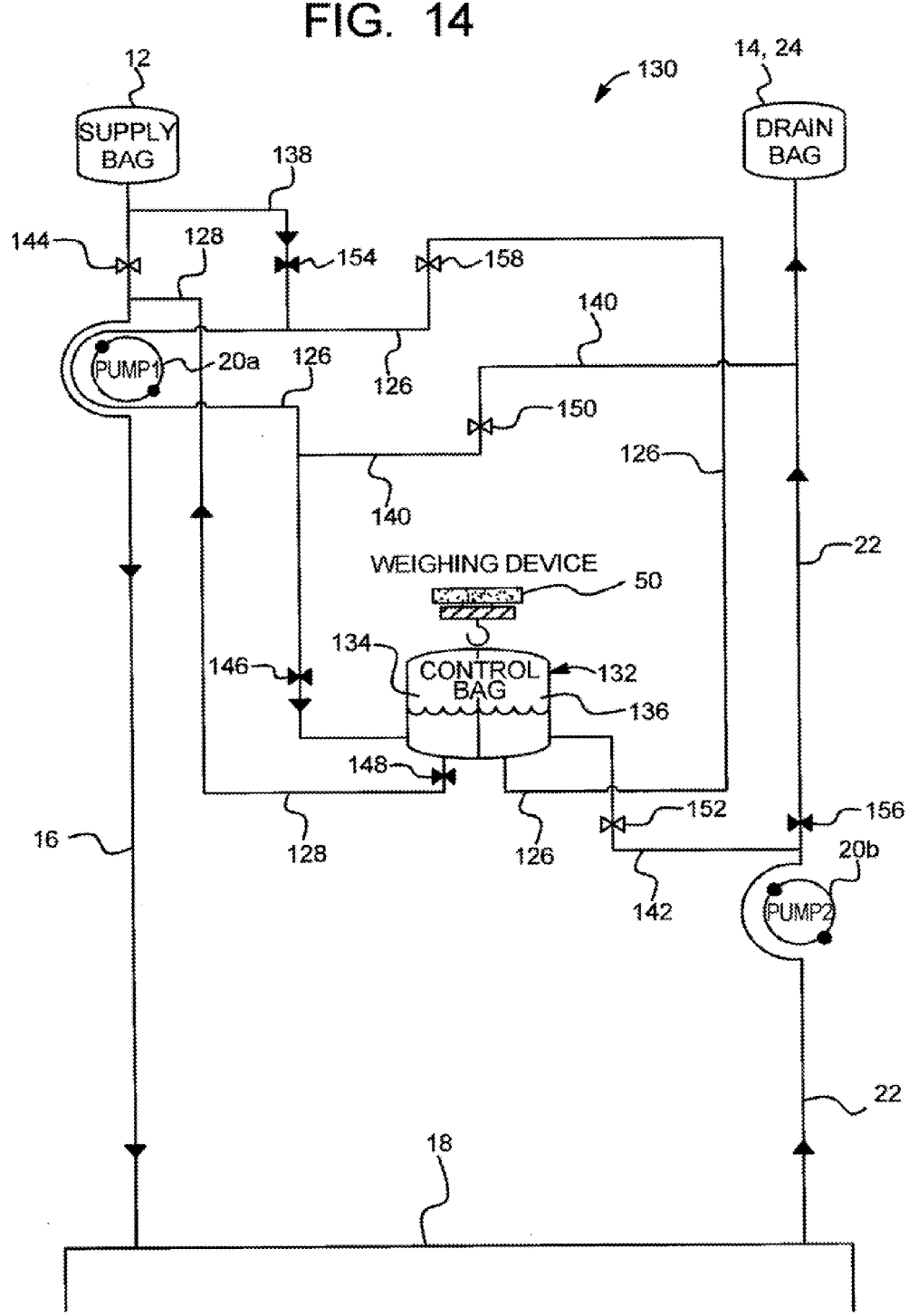
FIG. 14 is a schematic illustration of the kidney failure therapy weight balancing fluid control system of FIG. 12 in a second valve state.
Figure 15:
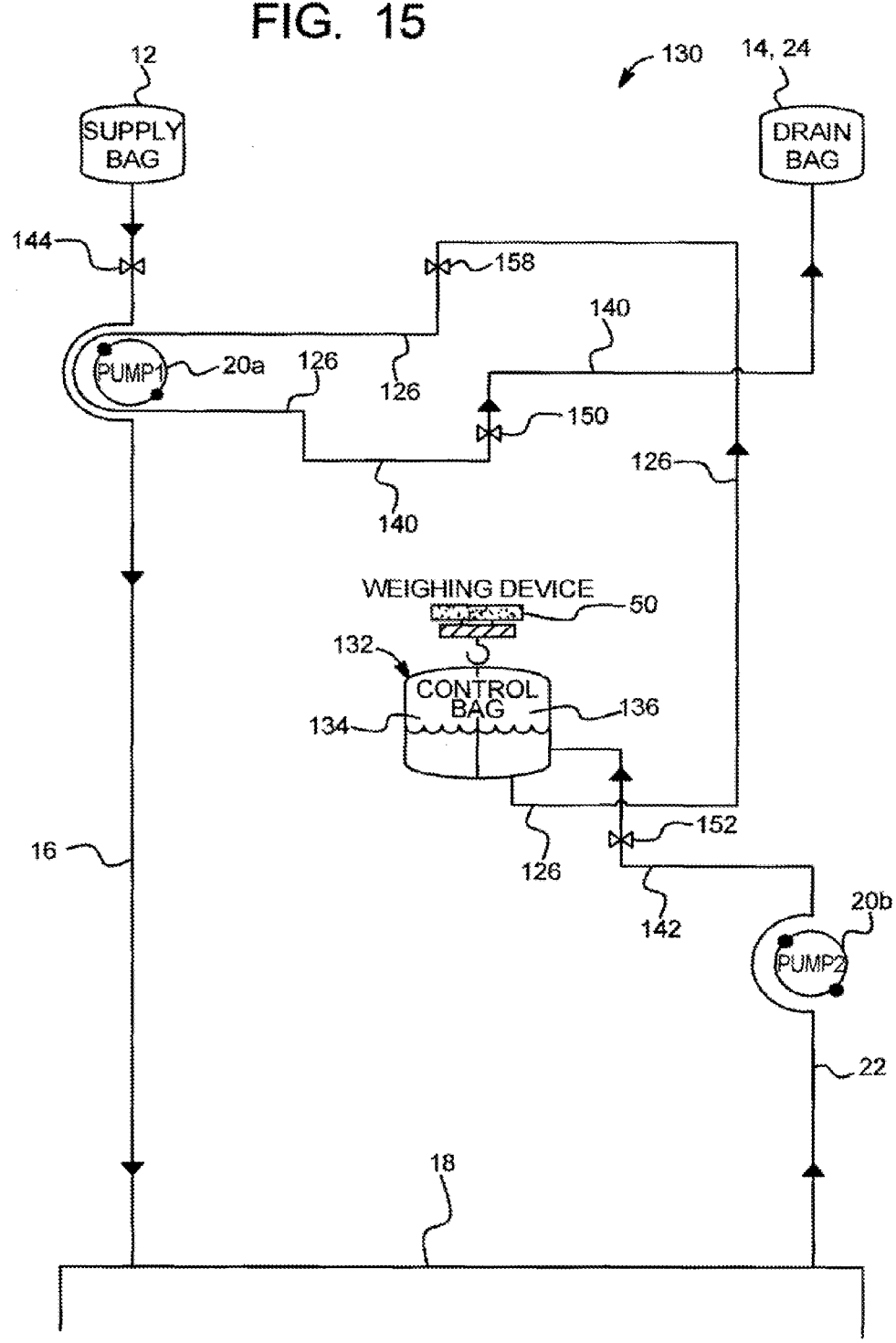
FIG. 15 is a schematic illustration of the kidney failure therapy weight balancing fluid control system of FIG. 14 in the second valve state with closed-off sections of the flow path eliminated for clarity.

FIGS. 14 and 15 illustrate system 130 in a second valve state. Here, loop 126 operating as the inner dual tube contacting pump 20a is used alternatively to pump used dialysate out of spent portion 136 of control bag 132 to drain. For purposes of illustration, FIG. 15 has removed the sections of the fluid loop that are not used in the second valve state. As seen best in FIG. 15, valves 144, 150, 152 and 158 are opened, while all other valves are closed. Pump 20a pumps fresh dialysate from supply bag 12, past valve 144, through the outer tubing segment operating with pump 20a, and through fresh supply line 16 to the inlet of filter 18. Simultaneously, pump 20a pumps fluid from the spent dialysate portion 136 of container 132, through line 126, past valve 158, through the inner tubing segment operating with pump 20a, into bypass line 140, past valve 150 and into drain bag 14 or house drain 24. Pump 20b pumps spent dialysate from filter 18, through line 22, through bypass line 142, past valve 152, and into spent dialysate portion 136 of bag 132.

The first valve state of FIGS. 12 and 13 enables blood clearance to occur during HD for example. The first valve state of FIGS. 12 and 13 also performs a calibration function because the weight of fluid in container 132 should remain constant theoretically regardless of the speed of pump 20a. This is because pump 20a pumps dialysate to and from fresh compartment 134 of container 132 at the same rate theoretically, while the weight of spent dialysate in compartment 136 remains unchanged. If the weight of dialysate increases in container 132, then pump 20a is pumping more fluid through line 126 than line 128/16. If the weight of dialysate decreases in container 132, then pump 20a is pumping more fluid through line 128/16 than line 126. The difference can be accounted for by adjusting the speed of pump 20b accordingly as described above.

Unless the system is to be run open loop, ultrafiltration should not occur during the first valve state of FIGS. 12 and 13 because there is no way for weighing device 50 to measure any differential weight gain between the rate of fluid entering or exiting filter 18. Accordingly, the first valve state may be used sparingly, only at the beginning or end of therapy, during a calibration mode, or at any time of a UF profile specifying a zero UF rate. The volume of spent portion 136 may therefore be correspondingly bigger than that of fresh portion 134 because in the second state of FIGS. 14 and 15, no fresh dialysate is pumped from or to fresh portion 134 of container 132.

The second valve state of FIGS. 14 and 15 enables blood clearance and ultrafiltration to occur during HD for example, taking into account the calibration information from the first valve state. In the second valve state, pump 20a removes spent dialysate from spent portion 136 of container 132 at the same rate theoretically that it pumps fluid into filter 18. Pump 20b pumps spent dialysate from filter 18 to spent portion 136 of container 132.

If the flow through segments of pump 20a is matched and the weight of dialysate increases in container 132, then pump 20b is removing a knowable amount of spent dialysate from the patient at a knowable rate. If the weight of dialysate decreases in container 132, then pump 20a is adding a knowable amount of fresh dialysate to the patient at a knowable rate. The rate at which fluid is accumulated in spent portion 136 of container 132 can correspond to a preset or variable UF rate. The second valve state of system 130 operates much the same as system 10 of FIGS. 1 and 2.

Referring now to FIGS. 16 to 19, yet another system including another apparatus and method for compensating between the differences in flow through the dual tubing segments operating with pump 20a is illustrated by system 160. System 160 includes many of the components already described herein, such as, supply 12, drain 14, 24, lines 16 and 22, filter 18, pumps 20a to 20c, weighing device 50, etc. For ease of illustration, control device 100 is again not shown, nor are the signal lines leading to control device 100 from weighing device 50, the output signal lines to pumps 20a to 20c, or the output signal lines to the valves shown in FIGS. 16 to 19. System 160 includes all such structures and can include pressure transducer(s), pressure regulator(s) and/or relief valve(s) in one or more suitable places as necessary.

One primary difference in system 160 is that the dual portion control container 132 discussed above in connection with system 130 is employed. Here again, control container 132 is divided into fresh and spent dialysate portions 134 and 136. The primary difference between system 160 and system 130 is that pump 20a is dedicated to driving fresh dialysate from supply 12 to filter 18. Third pump 20c is added to operate with loop 126.

In system 160, pump 20c is configured to pump either fresh dialysate through loop 126 to the inlet of fresh portion 134 of container 132 or spent dialysate from the outlet of spent portion 136 of container 132 to drain 14, 24. Loop 126 as illustrated is connected fluidly to the inlet of fresh portion 134 and the outlet of spent portion 136 of container 132.

System 160 includes the additional flow paths of system 130. Namely, fresh bypass supply line 138 is connected fluidly to line 16 (between supply 12 and pump 20a) and loop 126 (upstream of pump 20c). Fresh bypass return line 128 is connected fluidly to line 16 (between supply 12 and pump 20a) and to the outlet of fresh portion 134 of control container 132. Spent bypass supply line 142 is connected fluidly to drain line 22 (downstream of pump 20b) and to the inlet of spent portion 146 of control bag 132. Bypass line 140 is also connected between loop 126 (downstream of pump 20c) and drain line 22 (downstream of pump 20b).

System 160 also includes the additional valves of system 130. Valve 144 is coupled operably to fresh supply line 16 upstream of pump 20a. Valve 146 is coupled operably to loop 126 prior to the inlet of fresh portion 134 of bag 132. Valve 148 is coupled operably to fresh dialysate return line 128. Valve 150 is coupled operably to bypass line 140. Valve 152 is coupled operably to spent bypass supply line 142. Valve 154 is coupled operably to fresh bypass supply line 138. Valve 156 is coupled operably to dialysate line 22 downstream of pump 20b. Valve 158 is coupled operably to loop 126 upstream of pump 20a.

Figure 16:
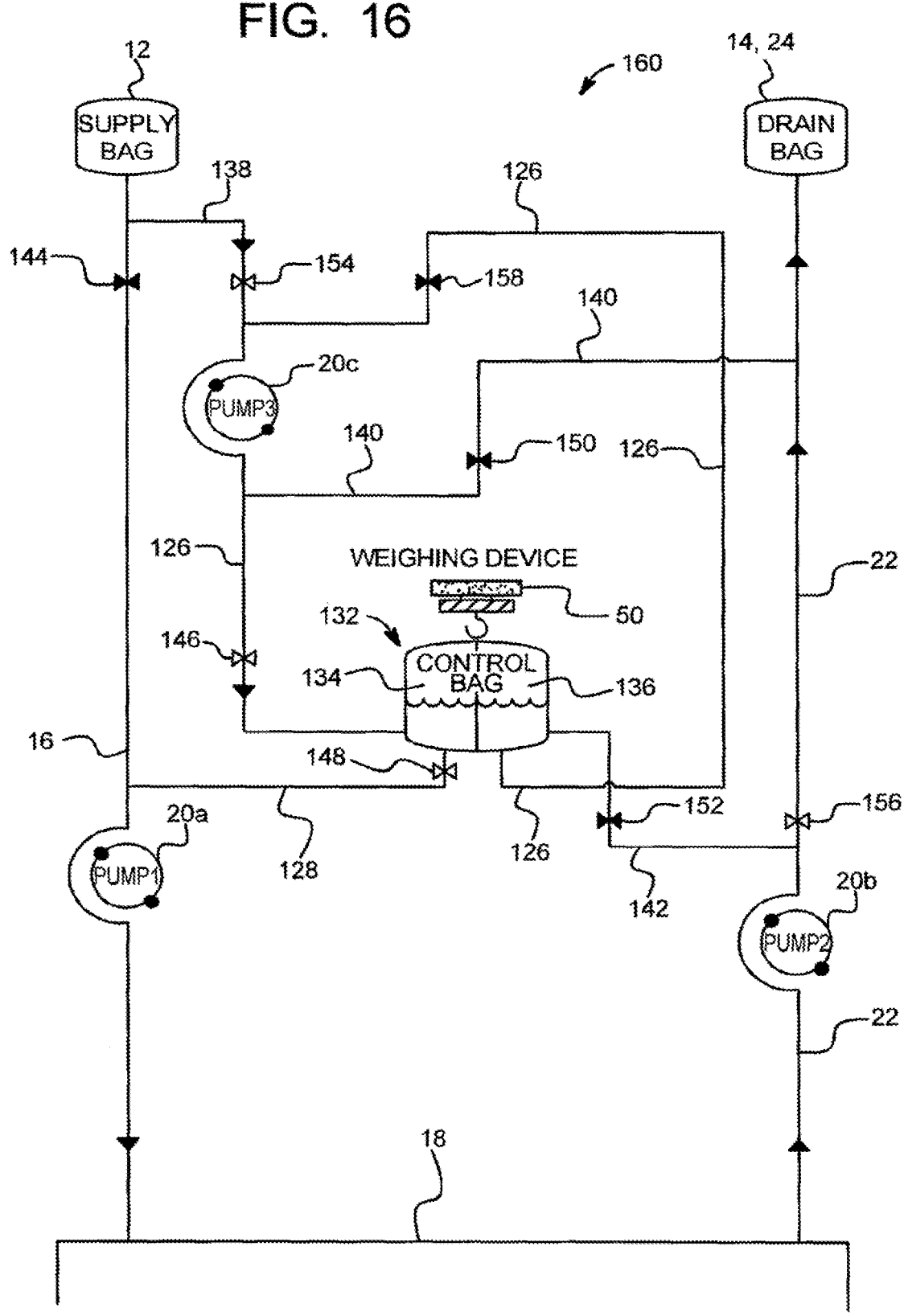
FIG. 16 is a schematic illustration of yet a further example of a kidney failure therapy weight balancing fluid control system in a first valve state, which has a third pump and a control container with separated fresh and spent portions.
Figure 17:
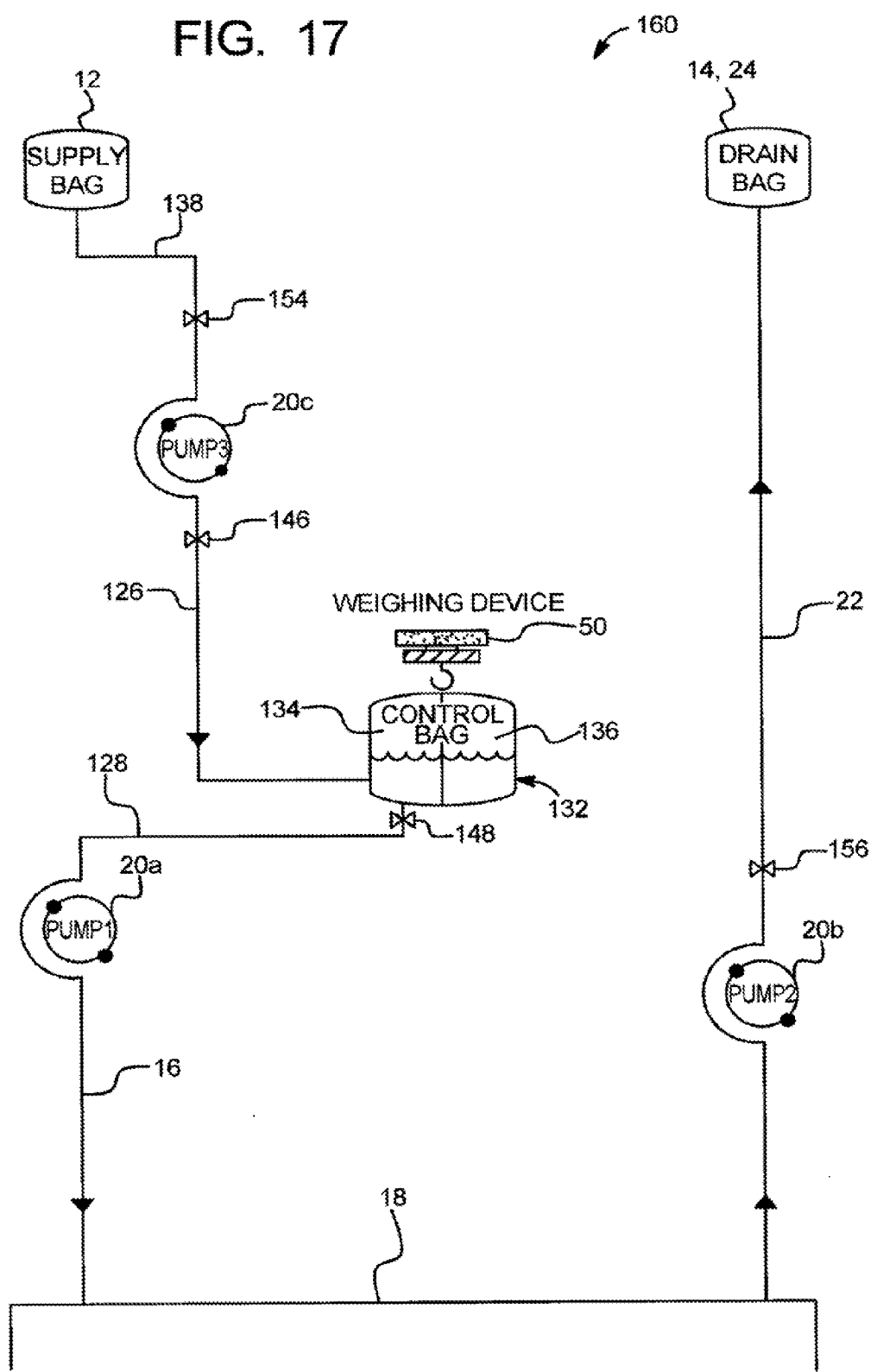
FIG. 17 is a schematic illustration of the kidney failure therapy weight balancing fluid control system of FIG. 16 in the first valve state with closed-off sections of the flow path eliminated for clarity.

FIGS. 16 and 17 show system 160 in a first valve state. Here, a portion of loop 126 is used with pump 20c to pump fresh dialysate into fresh chamber 134 of control container 132. For purposes of illustration, sections of the fluid loop that are not used in the valve state of FIG. 12 are removed in FIG. 13. In the first valve state of FIGS. 16 and 17, valves 146, 148, 154 and 156 are opened, while all other valves are closed. As seen most readily in FIG. 17, pump 20c pumps fresh fluid from supply 12, through line 138, past valve 154, through the portion of loop 126 shown in FIG. 17, past valve 146 and into fresh portion 134 of control bag 132. Here, Pump 20a pumps fresh fluid from fresh portion 134, through line 128, past valve 148, through line 16, to filter 18. At the same time, pump 20b pumps spent dialysate from filter or diffusion membrane 18, past valve 156, through line 22, to drain bag 14 or house drain 24.

Figure 18:
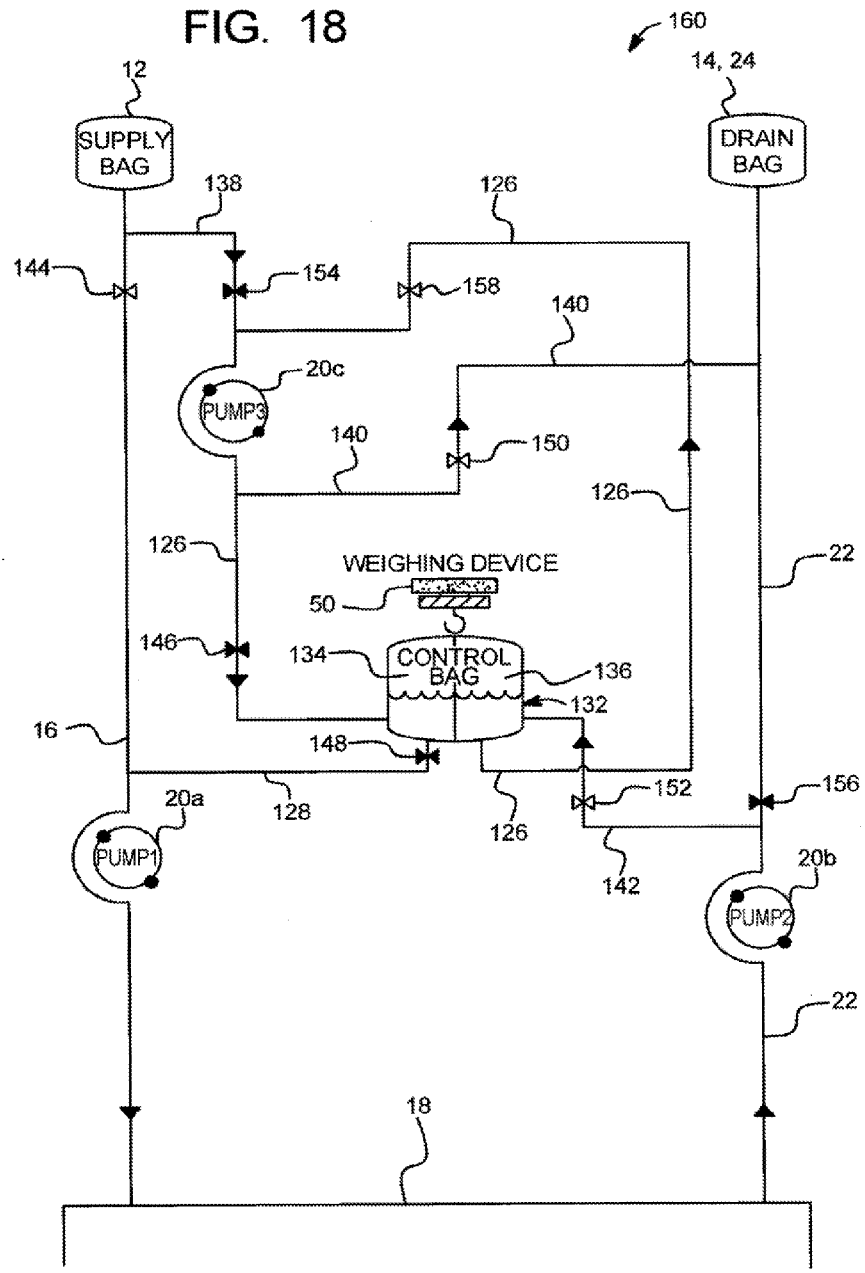
FIG. 18 is a schematic illustration of the kidney failure therapy weight balancing fluid control system of FIG. 16 in a second valve state.
Figure 19:
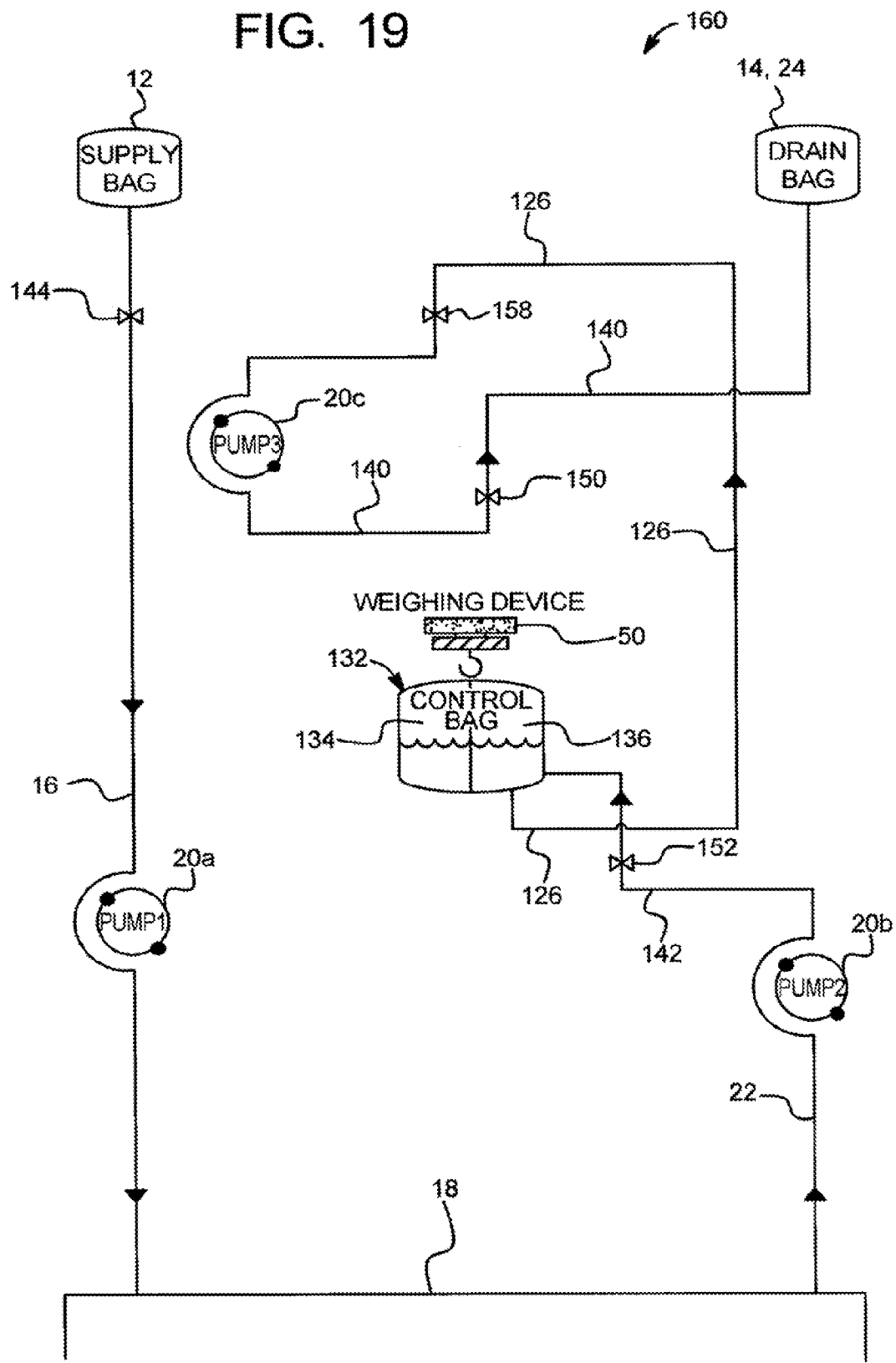
FIG. 19 is a schematic illustration of the kidney failure therapy weight balancing fluid control system of FIG. 18 in the second valve state with closed-off sections of the flow path eliminated for clarity.

FIGS. 18 and 19 illustrate system 160 in a second valve state. Here, loop 126 is used with 20c to pump used dialysate out of spent portion 136 of control bag 132. For purposes of illustration, FIG. 19 has removed the sections of the fluid loop that are not used in the second valve state. As seen best in FIG. 19, valves 144, 150, 152 and 158 are opened, while all other valves are closed. Pump 20a pumps fresh dialysate from supply bag 12, past valve 144, through fresh supply line 16, to the inlet of filter 18. Simultaneously, pump 20c pumps fluid from the spent dialysate portion 136, through line 126, past valve 158, through bypass line 140, past valve 150 and into drain bag 14 or house drain 24. Pump 20b pumps spent dialysate from filter 18, through line 22, through bypass line 142, past valve 152, and into spent dialysate portion 136 of bag 132.

In an open-loop arrangement, control device 100 in the first valve state can set pumps 20a to 20c to match the flow of fresh and spent dialysate fluid as best as possible during therapy. During therapy, control device 100 adjusts pump 20b to remove fluid from the patient according to a predetermined rate or UF profile. UF control can be accomplished by calculating theoretical flowrates for pumps 20b and 20a/20c and subtracting theoretical flowrate 20a/20c from theoretical flowrate 20b.

In a closed loop arrangement, in the first valve state of FIGS. 16 and 17, the speed of pump 20b is set to match the speed of pump 20c. To perform ultrafiltration, pump 20b (and thus pump 20c) is set at a higher speed than pump 20a to remove fluid from the patient according to a predetermined rate or UF profile. The difference in fluid pumped between pumps 20b and 20a is the same as the difference in fluid pumped between pumps 20c and 20a. The difference in fluid pumped between pumps 20c and 20a corresponds to a net gain in weight in fresh portion 134 of container 132, which is measured by weighing device 50. That net gain in weight corresponds to the amount of ultrafiltrate removed during the first valve state. The rate at which fluid is accumulated in fresh portion 134 of container 132 corresponds to the preset or variable UF rate. Any of the above-described calibration or during treatment embodiments for detecting and/or correcting for differences in flow produced by pump 20b versus pump 20c may be incorporated into system 130.

In the second valve state of FIGS. 18 and 19, the speed of pump 20a is set to match the speed of pump 20c. To perform ultrafiltration, pump 20b is set at a higher speed than pump 20a (and thus pump 20c) to remove fluid from the patient according to a predetermined rate or UF profile. The difference in fluid pumped between pumps 20b and 20a is the same as the difference in fluid pumped between pumps 20b and 20c. The difference in fluid pumped between pumps 20b and 20c results in a net gain in weight in spent portion 136 of container 132, which is measured by weighing device 50. That net gain in weight corresponds to the amount of ultrafiltrate removed during the second valve state. The rate at which fluid is accumulated in spent portion 136 of container 132 corresponds to the preset or variable UF rate. Any of the above-described calibration or during treatment embodiments for detecting and/or correcting for differences in flow produced by pump 20a versus pump 20c may be incorporated into system 130.

Referring now to FIGS. 20 to 22, three different embodiments for the weighing device/control bag configuration are illustrated. As used in any of the embodiments herein, weighing device 50 is used collectively to mean weighing device 50a in FIG. 20 and weighing device 50b in FIGS. 21 and 22. As has been described herein, weighing device 50 sends a signal 52 to control device 100 in each of the embodiments.

In FIG. 20, weighing device 50a includes a hook or other type of attachment member 162 from which control container 30 or 132 is hung. To that end, control container 30 or 132 can include a perforated tab or other type of attachment device configured and arranged to loop over or hook onto hook 162. In an embodiment, such perforated tab or attachment device is placed on control container 30 or 132 such that it tends to let container 30 or 132 hang evenly or in a centered positioned. Control container 30 or 132 in any of the embodiments described herein is a flexible bag or pouch sized to receive the initial amount of fluid plus the amount of ultrafiltrate produced during therapy. If a normal amount of ultrafiltrate is four liters, for example, then control container or control bag 30 or 132 can be sized to hold five or six liters of fluid, for example.

In FIG. 21, control bag 30 or 132 rests on a platform 164 of weighing device 50b. Here, control container 30, 132 is structurally rigid enough to support itself and the weight of dialysate collected within the container. In any case, container 30 or 132 can be made of a plastic or polymeric material, such as a clear or translucent material.

Referring now to FIG. 22, in an another embodiment a bin 166 is placed onto, attached to or formed integrally with platform 164. Control container 30 or 132 sits within and is supported by bin 166. Control container 30 or 132 therefore does not need the structural integrity of control container 30 or 132 of FIG. 21 and can instead be made of a flexible material that can deform within bin 166.

Figure 23:
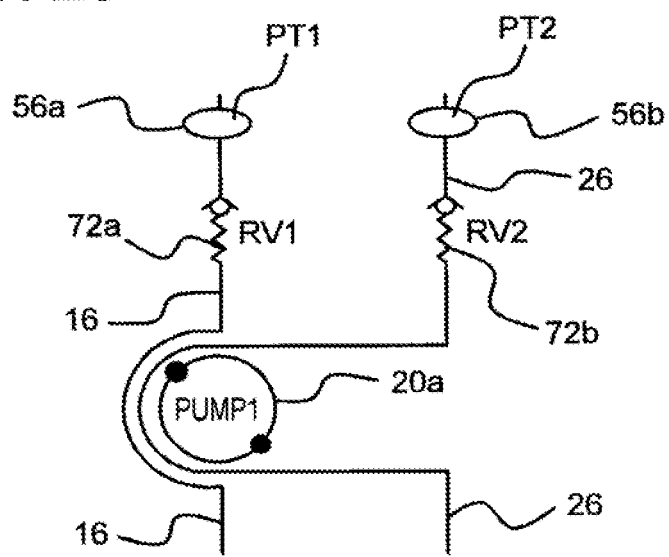
FIGS. 23 and 24 are schematic illustrations of pressure regulation apparatuses and methods.
Figure 24:
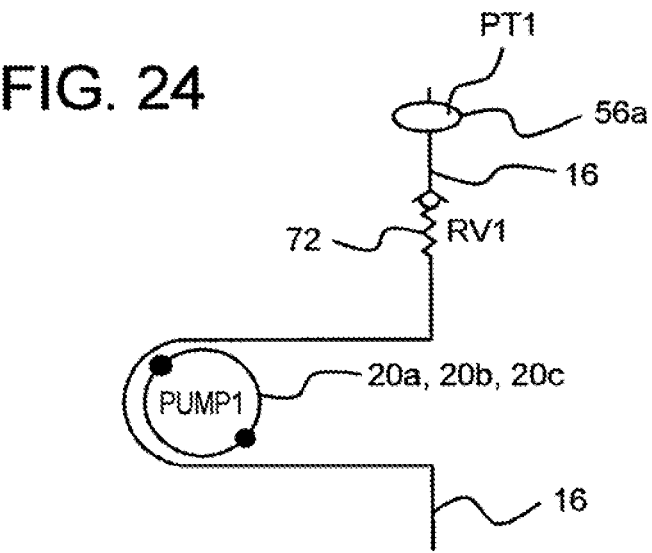

Referring now to FIGS. 23 and 24, in an embodiment, pressure regulators 72a/72b and/or pressure transducers 56a/56b are placed at the inlet of the dual segment or single segment pumping peristaltic pumps 20a to 20c to help ensure that different peristaltic pumps pump the same flow, at equal speeds, when desired. Such regulators 72a/72b and transducers 56a/56b also help to ensure that the single pump 20a operating dual pump segments of tubes 16 and 26 pumps the same flow at equal speeds. The pressure regulators 72a/72b and/or transducers 56a/56b are alternatively placed in any combination either upstream or downstream of any of the peristaltic pumps 20a to 20c in any of the embodiments described herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A kidney failure treatment system comprising:
a dialysate supply;
a weighing device;
a control container coupled operably to the weighing device, the control container divided into fresh dialysate and spent dialysate portions;
a membrane filter;
a drain;
first, second and third pumps;
a first fluid conduit coupled fluidly to the dialysate supply and the membrane filter, the first fluid conduit coupled operably to the first pump;
a second fluid conduit coupled fluidly to the membrane filter and the drain, the second fluid conduit coupled operably to the second pump; and
a third fluid conduit coupled fluidly to at least one of the fresh and spent portions of the control container, the third fluid conduit coupled operably to the third pump.

2. The kidney failure treatment system of claim 1, wherein the third fluid conduit is coupled fluidly to an inlet of the fresh portion of the control container, and which includes a fourth fluid conduit coupled fluidly to an outlet of the fresh portion.

3. The kidney failure treatment system of claim 2, wherein the fourth fluid conduit is coupled fluidly to the first fluid conduit.

4. The kidney failure treatment system of claim 1, wherein the third fluid conduit is coupled fluidly to an outlet of the spent portion of the control container, and which includes a fourth fluid conduit coupled fluidly to an inlet of the spent portion.

5. The kidney failure treatment system of claim 4, wherein the fourth fluid conduit is coupled fluidly to the second fluid conduit.

6. The kidney failure treatment system of claim 1, wherein at least one of the first, second and third fluid conduits is coupled physically to its respective first, second or third pump.

7. The kidney failure treatment system of claim 1, wherein the membrane filter is selected form the group consisting of: a dialyzer, a hemofilter and a patient's peritoneum.

8. The kidney failure treatment system of claim 1, which includes a fresh-portion-valve-state in which fresh dialysate can be pumped to and from the fresh portion of the control container.

9. The kidney failure treatment system of claim 8, wherein at least one of a spent-portion-inlet valve and a spent-portion-outlet valve is closed in the fresh-portion-valve-state.

10. The kidney failure treatment system of claim 8, wherein at least one of: (i) the first pump is configured to pump fresh dialysate from the fresh portion; (ii) the second pump is configured to pump spent fluid from the membrane filter; and (iii) the third pump is configured to pump fresh fluid to the fresh portion in the fresh-portion-valve-state.

11. The kidney failure treatment system of claim 8, which includes a spent-portion-valve-state in which spent dialysate can be pumped to and from the spent portion of the control container.

12. The kidney failure treatment system of claim 1, which includes a spent-portion-valve-state in which spent dialysate can be pumped to and from the spent portion of the control container.

13. The kidney failure treatment system of claim 12, wherein at least one of a fresh-portion-inlet valve and a fresh-portion-outlet valve is closed in the spent-portion-valve-state.

14. The kidney failure treatment system of claim 12, wherein at least one of: (i) the first pump is configured to pump fresh dialysate from the dialysate supply to the membrane filter; (ii) the second pump is configured to pump spent dialysate from the membrane filter to the spent portion; and (iii) the third pump is configured to pump fluid from the spent portion to the drain during the spent-portion-valve-state.

15. The kidney failure treatment system of claim 1, wherein the dialysate supply includes at least one of: a container of fresh dialysate and an online dialysate generation source.

16. A kidney failure treatment system comprising:
a dialysate supply;
a weighing device;
a control container coupled operably to the weighing device;
a membrane filter;
a drain;
first, second and third pumps;
a first fluid conduit coupled fluidly to the dialysate supply and the membrane filter, the first fluid conduit coupled operably to the first pump;
a second fluid conduit coupled fluidly to the membrane filter and the control container, the second fluid conduit coupled operably to the second pump; and
a third fluid conduit coupled fluidly to the control container and the drain, the third fluid conduit coupled operably to the third pump.

17. The kidney failure treatment system of claim 16, which includes a logic implementor coupled operably to the weighing device, the logic implementor configured to cause at least one of: (i) flow through the first fluid conduit to at least substantially match flow through the third fluid conduit; and (ii) flow through the second fluid conduit to be set to remove a desired amount of fluid from a patient.

18. The kidney failure treatment system of claim 16, which includes a logic implementor coupled operably to the first, second and third pumps, the logic implementor configured to cause the first, second and third pumps to perform at least one of: (i) at least substantially match flow through the first and third fluid conduits; and (ii) remove a desired amount of fluid from a patient via the second fluid conduit.

19. The kidney failure treatment system of claim 16, wherein at least one of the first, second and third pumps is of a type selected from the group consisting of: a peristaltic pump and a membrane pump.

20. The kidney failure treatment system of claim 16, wherein the membrane filter is selected form the group consisting of: a dialyzer, a hemofilter and a patient's peritoneum.

* * * * *

UNITED STATES PATENT AND TRADEMARK OFFICE
CERTIFICATE OF CORRECTION

PATENT NO. : 8,562,823 B2
APPLICATION NO. : 13/864921
DATED : October 22, 2013
INVENTOR(S) : Roger et al.

It is certified that error appears in the above-identified patent and that said Letters Patent is hereby corrected as shown below:

In the Specification:

In Column 2, line 38, replace "though" with --through--.

In Column 4, line 20, replace "(("PD")" with --("PD")--.

In Column 4, line 23, replace "modalities)" with --modalities--.

In Column 5, line 36, replace "with a valving" with --with valving--.

In Column 6, line 38, replace "to filter" with --to the filter--.

In Column 8, line 41, replace "("PD,"" with --("PD"),--.

In Column 8, line 44, replace "modalities)" with --modalities--.

In Column 10, line 1, replace "the particular" with --in particular--.

In Column 10, line 15, replace "continues" with --continuous--.

In Column 10, line 19, replace "bags, a large" with --bags, or a large--.

In Column 10, lines 20-21, replace "can any" with --can be any--.

In Column 11, lines 51-52, replace "20a for example" with --20a, for example,--.

In Column 11, line 57, replace "Here, length" with --Here, the length--.

In Column 14, line 13, replace "weight would be measured" with --weight measured--.

Signed and Sealed this
Fifteenth Day of April, 2014

Michelle K. Lee
*Deputy Director of the United States Patent and Trademark Office*

CERTIFICATE OF CORRECTION (continued)
U.S. Pat. No. 8,562,823 B2

In the Specification:

In Column 14, lines 14-15, replace "FIG. 5 it should be appreciated" with --FIG. 5, it should be appreciated,--.

In Column 14, line 24, replace "then" with --than--.

In Column 15, line 35, replace "herein" with --herein.--.

In Column 16, line 44, replace "flow the" with --flow of the--.

In Column 16, line 46, replace "as," with --as--.

In Column 20, line 51, replace "positioned" with --position--.